United States Patent
Cushing et al.

(10) Patent No.: US 6,835,726 B2
(45) Date of Patent: Dec. 28, 2004

(54) PYRIMIDINE DERIVATIVES

(75) Inventors: Timothy D. Cushing, Pacifica, CA (US); Heather L. Mellon, Limerick, PA (US); Juan C. Jaen, Burlingame, CA (US); John A. Flygare, Burlingame, CA (US); Shi-Chang Miao, Foster City, CA (US); Xiaoqi Chen, San Mateo, CA (US); Jay P. Powers, Pacifica, CA (US)

(73) Assignee: Amgen Inc., San Francisco, CA (US)

( * ) Notice: Subject to any disclaimer, the term of this patent is extended or adjusted under 35 U.S.C. 154(b) by 0 days.

(21) Appl. No.: 10/350,801

(22) Filed: Jan. 24, 2003

(65) Prior Publication Data

US 2004/0006068 A1 Jan. 8, 2004

Related U.S. Application Data

(63) Continuation of application No. 09/737,983, filed on Dec. 15, 2000, now Pat. No. 6,528,513, which is a continuation of application No. 09/249,641, filed on Feb. 12, 1999, now Pat. No. 6,200,977.
(60) Provisional application No. 60/075,005, filed on Feb. 17, 1998.

(51) Int. Cl.[7] ..................... A61K 31/33; A61K 31/505; C07D 239/00; C07D 487/00; C07D 207/00
(52) U.S. Cl. ..................... 514/183; 514/256; 514/269; 514/275; 514/396; 514/315; 514/408; 514/422; 544/242; 544/255; 544/256; 544/262; 544/264; 544/299; 544/323; 548/400; 548/517; 548/518
(58) Field of Search ................... 514/183, 256, 514/269, 275, 396, 315, 408, 422; 544/242, 255, 262, 264, 299, 323, 326; 548/400, 517, 518

(56) References Cited

U.S. PATENT DOCUMENTS

| | | | |
|---|---|---|---|
| 3,178,432 A | 4/1965 | Druey et al. | 260/256.2 |
| 4,698,340 A | 10/1987 | Takaya et al. | 514/222 |
| 4,788,195 A | 11/1988 | Torley et al. | 514/252 |
| 4,929,726 A | 5/1990 | Strekowski et al. | 514/122 |
| 4,983,608 A | 1/1991 | Effland et al. | 514/256 |
| 4,987,146 A | 1/1991 | Rohde et al. | 514/228.2 |
| 5,147,876 A | 9/1992 | Mizuchi et al. | 514/275 |
| 5,223,505 A | 6/1993 | Hargreaves et al. | 514/275 |
| 5,304,647 A | 4/1994 | Strekowski et al. | 544/235 |
| 5,525,724 A | 6/1996 | Hunds | 544/334 |
| 6,200,977 B1 * | 3/2001 | Cushing et al. | 514/252.14 |
| 6,528,513 B2 * | 3/2003 | Cushing et al. | 514/252.19 |

FOREIGN PATENT DOCUMENTS

| | | | |
|---|---|---|---|
| DE | 23 41 925 A1 | | 3/1975 |
| DE | 143 615 | | 9/1980 |
| EP | 605031 | * | 7/1994 |
| EP | 0 640 599 A | | 3/1995 |
| EP | 0 806 418 A | | 11/1997 |
| WO | 9505378 | * | 2/1995 |
| WO | 9709325 | * | 3/1997 |
| WO | WO 98 23597 A | | 6/1998 |

OTHER PUBLICATIONS

Debnath et al, J. Med. Chem.,42,3203–9(1999).*
Chemical Abstract DN 121:230775, also cited as EP 605031.*
Chemical AbstractDN 123:55866, also cited as WO 9505378.*
Chemical Abstract DN 126:264109, also cited asWO 9709325.*
Agrawal et al,Expert Opinion Ther. Targets 5/3,303–326(2001).*
Verani et al, PunMed Abstract 12462390, also cited as Curr.Mol.Med.2/8,691–702(2002).*
Target et al,Bioorgnic & Medicinal Chem. Letters, 11,2143–46(2001).*
Chem. Pharm. Bull; Keda et al.; 44/9,1700; Sythe. & cytoprotective anticulcer activ. of pyrim.

* cited by examiner

*Primary Examiner*—Richard Raymond
*Assistant Examiner*—Sudhaker B. Patel
(74) *Attorney, Agent, or Firm*—Townsend and Townsend and Crew LLP

(57) ABSTRACT

Compounds and compositions are provided which are useful for the treatment of viral infections, particularly human Cytomegalovirus infection. The compounds include novel pyrimidine-based derivatives.

12 Claims, 18 Drawing Sheets

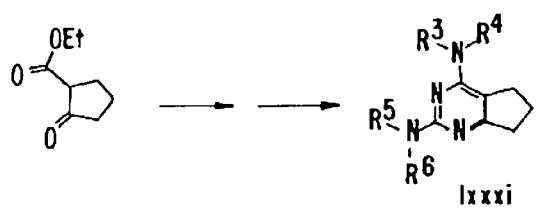
*FIG. IIC.*
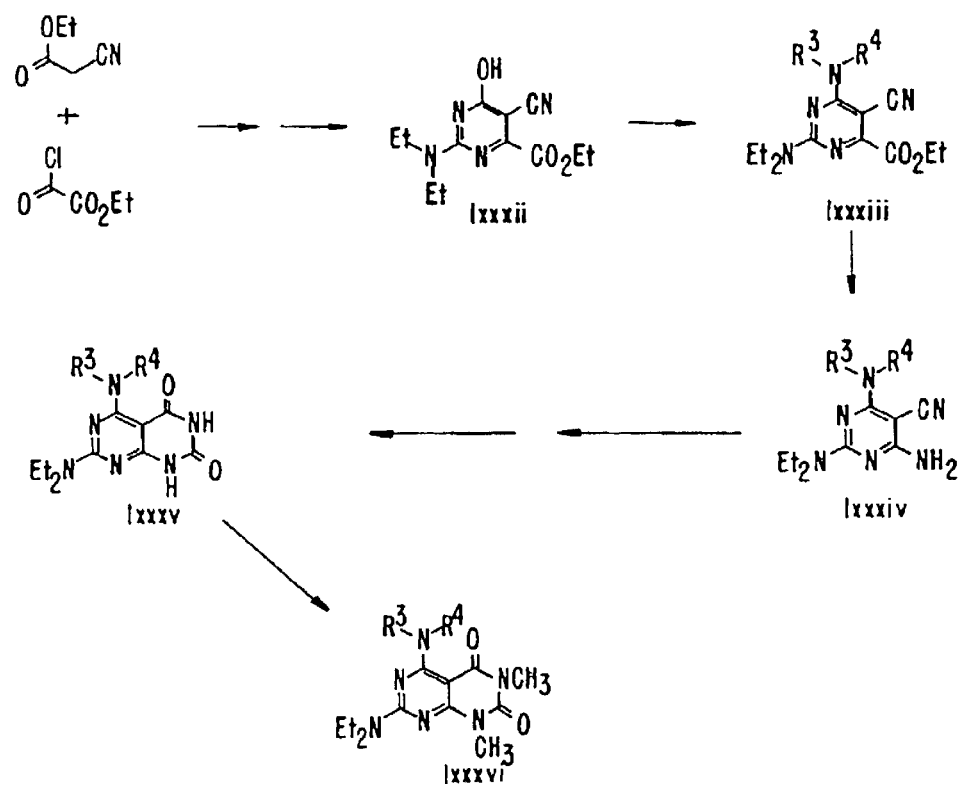
*FIG. IID.*

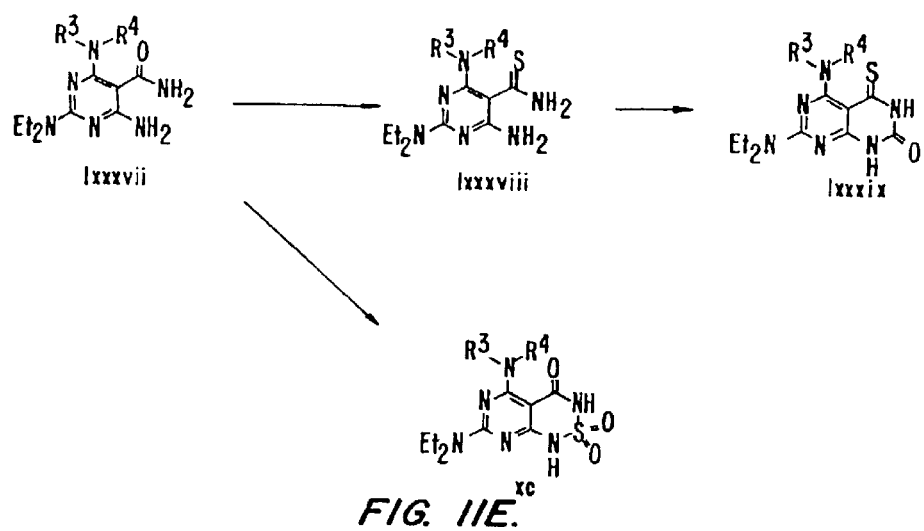
*FIG. 11E.*
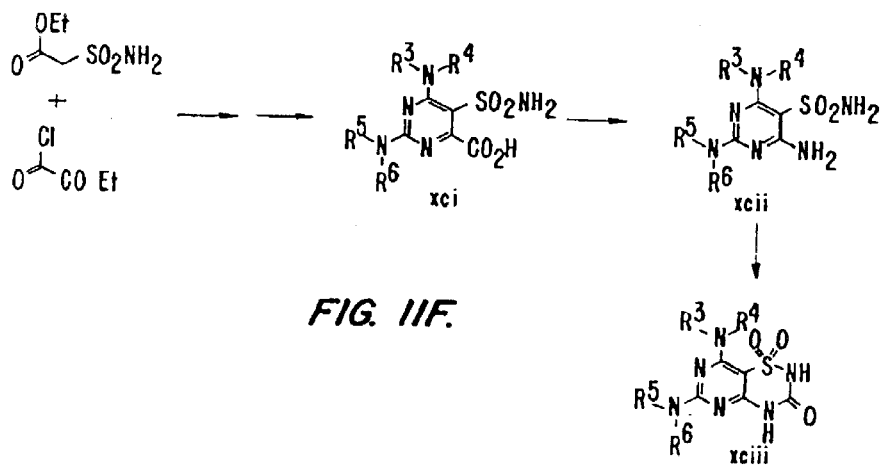
*FIG. 11F.*
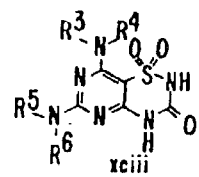

PYRIMIDINE DERIVATIVES

CROSS-REFERENCE TO RELATED APPLICATION

This application is a continuation of U.S. application Ser. No. 09/737,983, filed Dec. 15, 2000, now issued as U.S. Pat. No. 6,528,513, which is a continuation of U.S. application Ser. No. 09/249,641, filed Feb. 12, 1999, now issued as U.S. Pat. No. 6,200,977, which is related to PCT/US99/03136, and also claims benefit of priority to U.S. Provisional Application No. 60/075,005, filed Feb. 17, 1998, the disclosure of each being incorporated by reference.

STATEMENT REGARDING FEDERALLY SPONSORED RESEARCH

The invention described herein was not made with the aid of any federally sponsored grants.

FIELD OF THE INVENTION

The field of the invention is in novel substituted pyrimidine compounds and their use as pharmacologically active agents capable of suppressing and inhibiting viruses (e.g., herpes viruses). The subject compounds and compositions are particularly useful in treating and suppressing human Cytomegalovirus.

BACKGROUND OF THE INVENTION

Cytomegalovirus (CMV) is a member of the herpes virus family. Other well-known members of the herpes virus family include, for example, herpes simplex virus, types I and II, Epstein-Barr virus and varicella zoster virus. These viruses are related taxonomically, but each manifests in a clinically distinct manner. In the case of CMV, medical conditions arising from congenital infection include jaundice, respiratory distress and convulsive seizures which may result in mental retardation, neurologic disability or death. Infection in adults is frequently asymptomatic, but may manifest as mononucleosis, hepatitis, pneumonitis or retinitis, particularly in immunocompromised patients such as AIDS sufferers, chemotherapy patients, and organ transplant patients undergoing tissue rejection therapy.

A variety of drugs have been developed to treat herpes virus infections, including naturally occurring proteins and synthetic nucleoside analogs. For example, the natural antiviral protein interferon has been used in the treatment of herpes virus infections, as have the nucleoside analogs cytosine-arabinoside, adenine-arabinoside, iodoxyuridine and acyclovir, which is presently the treatment of choice for herpes simplex type II infection.

Unfortunately, drugs such as acyclovir that have proven sufficiently effective to treat infection by certain herpes viruses are not sufficiently effective to treat CMV. Additionally, drugs currently used to treat CMV infection, such as 9-((1,3-dihydroxy-2-propoxy)methyl)guanidine (ganciclovir, DHPG) and phosphonoformic acid (foscarnet), lack the acceptable side effect and safety profiles of the drugs approved for treatment of other herpes viruses. Moreover, such drugs are ineffective to treat certain strains of CMV that have acquired drug resistance. Thus, despite advances in the development of anti-herpes virus drugs, there remains a need for therapeutic agents effective in treating CMV infection with an increased safety margin. The present invention provides such therapeutic agents in the form of surprisingly effective substituted pyrimidine compounds.

SUMMARY OF THE INVENTION

The present invention provides novel substituted pyrimidine compounds. The compounds have the general formula I:

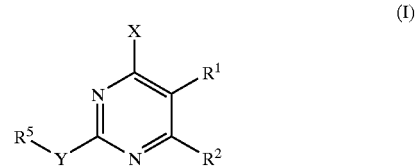

in which X represents $-NR^3R^4$, $-OR^3$, $-SR^3$, aryl, alkyl or arylalkyl. The letter Y represents a covalent bond, $-N(R^6)-$, $-O-$, $-S-$, $-C(=O)-$ or an alkylene group. $R^1$ and $R^2$ are independently selected from hydrogen, alkyl, $-O$-alkyl, $-S$-alkyl, aryl, arylalkyl, $-O$-aryl, $-S$-aryl, $-NO_2$, $-NR^7R^8$, $-C(O)R^9$, $-CO_2R^{10}$, $-C(O)NR^7R^8$, $-N(R^7)C(O)R^9$, $-N(R^7)CO_2R^{11}$, $-N(R^9)C(O)NR^7R^8$, $-S(O)_mNR^7R^8$, $-S(O)_nR^9$, $-CN$, halogen, and $-N(R^7)S(O)_mR^{11}$. The groups $R^3$ and $R^4$ are independently selected from hydrogen, alkyl, aryl or arylalkyl, or, when X is $-NR^3R^4$, $R^3$ and $R^4$ taken together with the nitrogen atom to which each is attached form a 5-, 6- or 7-membered aromatic or nonaromatic ring containing from one to three heteroatoms in the ring. $R^5$ and $R^6$ are independently hydrogen, alkyl, aryl or arylalkyl. $R^7$ and $R^8$ are each independently hydrogen, alkyl, aryl or arylalkyl, or, when attached to the same nitrogen atom can be combined with the nitrogen atom to form a 4-, 5-, 6-, 7- or 8-membered ring containing from one to three heteroatoms in the ring. $R^9$ and $R^{10}$ are independently selected from hydrogen, alkyl, aryl and arylalkyl. $R^{11}$ is selected from alkyl, aryl and arylalkyl. The subscript m is an integer of from 1 to 2 and the subscript n is an integer of from 1 to 3.

In addition to the above descriptions of $R^1$ to $R^{11}$, the formula above is meant to represent a number of compounds in which a second ring is fused to the pyrimidine ring. For example, $R^1$ can be joined to $R^2$, $R^1$ can be joined to $R^3$, $R^3$ can be joined to $N^3$ (the nitrogen atom at the 3-position of the pyrimidine ring), $R^5$ can be joined to $N^3$, $R^5$ can be joined to $N^1$ (the nitrogen atom at the 1-position of the pyrimidine ring) or $R^2$ can be joined to $N^1$ to form a fused 5-, 6-, or 7-membered ring.

Finally, the compounds of the present invention will typically have a molecular weight of from about 150 to about 750. The compounds provided in the above formula are meant to include all pharmaceutically acceptable salts thereof.

The compounds of the present invention are useful in therapeutic as well as prophylactic and diagnostic applications. Still further, the compounds are useful in the development of additional therapeutic agents as standards in a variety of assay formats. Accordingly, the present invention provides compositions containing the above compounds and pharmaceutically acceptable excipients or diagnostically acceptable excipients. The invention further provides methods of inhibiting or suppressing certain viruses, and methods of treating individuals infected with such viruses, particularly CMV. In addition to treatments for existing conditions, the present invention also provides methods for prophylactic treatments to prevent the onset of viral infection in patients undergoing, for example, organ transplants.

Other objects, features and advantages of the present invention will become apparent to those skilled in the art from the following description and claims.

DETAILED DESCRIPTION OF THE INVENTION

Abbreviations and Definitions

Figure 1:
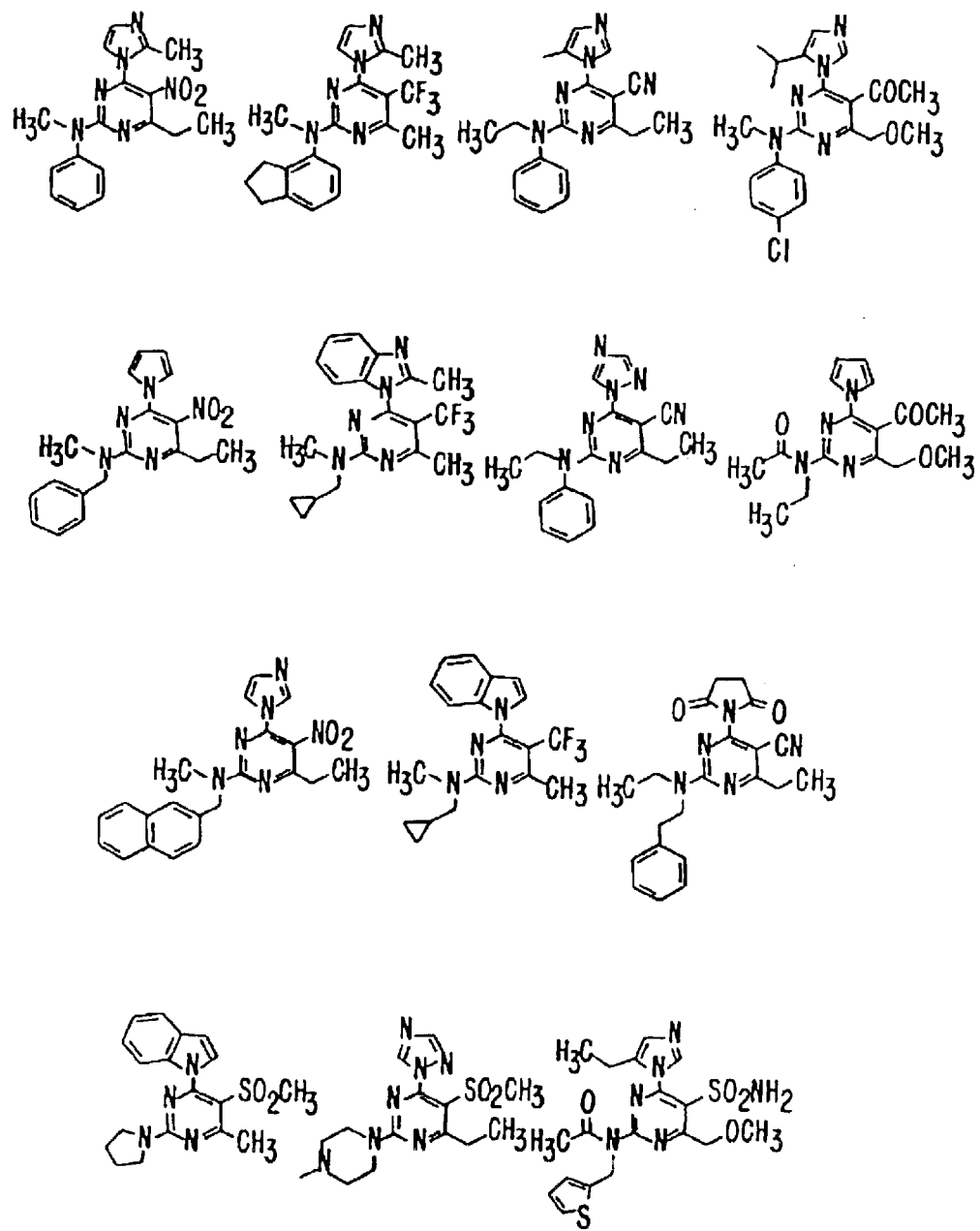
FIG. 1 provides the structures of exemplary compounds of formula IIa.

The term "alkyl," by itself or as part of another substituent, means, unless otherwise stated, a straight or branched chain or cyclic hydrocarbon radical or combinations thereof, which may be fully saturated, mono- or polyunsaturated and can include di- and multi-radicals, having the number of carbon atoms designated (i.e. C1–C10 means one to ten carbons). Examples of saturated hydrocarbon radicals include straight or branched chain groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. Other saturated hydrocarbon radicals include cyclopropylmethyl, cyclohexylmethyl and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those-derivatives of alkyl defined below as heteroalkyl, alkylene, heteroalkylene, cycloalkyl and heterocycloalkyl. Typically, an alkyl group will have from 1 to 24 carbon atoms, with those groups having 10 or fewer carbon atoms being preferred in the present invention. The term "alkylene" by itself or as part of another substituent means a divalent radical derived from an alkane, as exemplified by —CH$_2$CH$_2$CH$_2$CH$_2$—. A "lower alkyl" or "lower alkylene" is a shorter chain alkyl or alkylene group, generally having eight or fewer carbon atoms. Unless otherwise indicated, the alkyl groups can be unsubstituted or substituted by the substituents indicated below.

The term "heteroalkyl," by itself or in combination with another term, means, unless otherwise stated, a stable straight or branched chain radical consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. The term "heteroalkylene" by itself or as part of another substituent means a divalent radical derived from heteroalkyl, as exemplified by —CH$_2$—CH$_2$—S—CH$_2$CH— and —CH$_2$—S—CH$_2$—CH$_2$—.

The terms "cycloalkyl" and "heterocycloalkyl", by themselves or in combination with other terms, represent, unless otherwise stated, cyclic versions of "alkyl" and "heteroalkyl", respectively. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl. More particularly, the term "fluoroalkyl" also includes perfluoroalkyl, in which each hydrogen present in an alkyl group has been replaced by a fluorine.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quaternized. Non-limiting examples of aryl groups include phenyl, 1-naphthyl, 2-naphthyl, biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below.

As used herein, the term "bicyclic fused aryl-cycloalkyl" refers to those groups in which an aryl ring (or rings) is fused to a cycloalkyl group (including cycloheteroalkyl groups). The group can be attached to the remainder of the molecule through either an available valence on the aryl portion of the group, or an available valence on the cycloalkyl portion of the group. Examples of such bicyclic fused aryl-cycloalkyl groups are: indanyl, benzotetrahydrofuranyl, benzotetrahydropyranyl and 1,2,3,4-tetrahydronaphthyl.

Each of the above terms (e.g., "alkyl" and "aryl" and "bicyclic fused aryl-cycloalkyl") will typically include both substituted and unsubstituted forms of the indicated radical. Preferred substituents for each type of radical are provided below. In the case of radicals containing both aryl (including heteroaryl) and alkyl (including, for example, heteroalkyl, cycloalkyl, and cycloheteroalkyl) portions, each of the portions can be substituted as indicated.

Substituents for the alkyl groups (including those groups often referred to as alkenyl, heteroalkyl, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halo, —SiR'R"R'", —OC(O)R', —CO$_2$R', —CONR'R", —OC(O)NR'R", —NR"C(O)R', —NR"—C(O)—OR', —NH—C(NH$_2$)=NH, —NR'C(NH$_2$)=NH, —NH—C (NH$_2$)=NR', —S(O)R', —S(O)$_2$R', —S(O)$_2$NR'R", —CN and —NO$_2$ in a number ranging from zero to (2N+1), where N is the total number of carbon atoms in such radical. R', R" and R'" each independently refer to a hydrogen or C1–C10 alkyl group. Preferably, a substituted alkyl group will have from one to six independently selected substituents. More preferably, a substituted alkyl group will have from one to four independently selected substituents. Nevertheless, certain substituted alkyl groups (e.g., perfluoroalkyl) will have a full 2N+1 substituents (where N is the number of carbon atoms in a saturated alkyl group). Examples of substituted alkyl groups include: —C(O)—CH$_3$, —C(O)CH$_2$OH, —CH$_2$—CH(CO$_2$H)—NH$_2$ and —Si(CH$_3$)$_2$—CH$_2$—C(O)—NH$_2$.

Similarly, substituents for the aryl groups are varied and are selected from: -halo, —OR', —OC(O)R', —NR'R", —SR', —R', —CN, —NO$_2$, —CO$_2$R', —CONR'R", —OC(O)NR'R", —NR"C(O)R', —NR"—C(O)—OR', —NH—C (NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C1–C4)alkoxy, and perfluoro(C1–C4)alkyl, in a number ranging from zero to the total number of open valences on the aromatic ring system; and where R' and R" are independently selected from hydrogen, (C1–C8)alkyl, aryl, aryl-(C1–C4)alkyl, and aryloxy-(C1–C4)alkyl.

Two of the substituents on adjacent atoms of the aryl ring may optionally be replaced with a substituent of the formula —T—C(O)—(CH$_2$)$_s$—U—, wherein T and U are independently —NH—, —O—, —CH$_2$— or a single bond, and the subscript s is an integer of from 0 to 2. Alternatively, two of the substituents on adjacent atoms of the aryl ring may optionally be replaced with a substituent of the formula —A—(CH$_2$)$_p$—B—, wherein A and B are independently —CH$_2$—, —O—, —NH—, —S—, —S(O)—, —S(O)$_2$—, —S(O)$_2$NR'— or a single bond, and p is an integer from 1 to 3. One or more of the single bonds of the new ring so formed may optionally be replaced with a double bond. Alternatively, two of the substituents on adjacent atoms of the aryl ring may optionally be replaced with a substituent of the formula —(CH$_2$)$_q$—Z—(CH$_2$)$_r$—, where q and r are independently integers of from 1 to 3, and Z is —O—, —NR'—, —S—, —S(O)—, —S(O)$_2$—, or —S(O)$_2$NR'—. The substituent R' in —NR'— and —S(O)$_2$NR'— is selected from hydrogen or (C1–C6)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide a compound of formula I.

Certain compounds of the present invention can exist in unsolvated forms as well as solvated forms, including hydrated forms. In general, the solvated forms are equivalent to unsolvated forms and are intended to be encompassed within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Embodiments of the Invention

Compounds

In one aspect, the present invention provides compounds of general formula I:

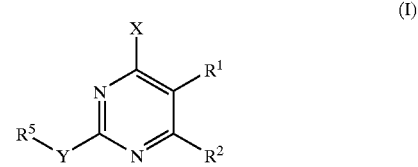

(I)

in which X represents —NR$^3$R$^4$, —OR$^3$, —SR$^3$, aryl, alkyl or arylalkyl. The letter Y represents a covalent bond, —N(R$^6$)—, —O—, —S—, —C(=O)— or an alkylene radical. Preferably, Y is —N(R$^6$)— or —O—, in which R$^6$ is as defined below. More preferably, Y is —N(R$^6$)—. For those embodiments in which Y is an alkylene radical, the alkylene radical will typically have from 1 to 8 carbon atoms in the chain, with alkylene groups having from 1 to 3 carbon atoms being preferred.

$R^1$ and $R^2$ are independently selected from hydrogen, alkyl, —O-alkyl, —S-alkyl, aryl, arylalkyl, —O-aryl, —S-aryl, —NO$_2$, —NR$^7$R$^8$, —C(O)R$^9$, —CO$_2$R$^{10}$, —C(O)NR$^7$R$^8$—N(R$^7$)C(O)R$^9$, —N(R$^7$)CO$_2$R$^{11}$, —N(R$^9$)C(O)NR$^7$R$^8$, —S(O)$_m$NR$^7$R$^8$, —S(O)$_n$R$^9$, —CN, halogen, or —N(R$^7$)S(O)$_m$R$^{11}$, in which R$^7$, R$^8$, R$^9$, R$^{10}$ and R$^{11}$ are as defined below.

In one group of preferred embodiments, $R^1$ is an electron-withdrawing group and $R^2$ is an electron-donating group. Within this group of embodiments, $R^1$ is preferably —NO$_2$, —S(O)$_m$NR$^7$R$^8$, —S(O)$_n$R$^9$, —CN, halogen, fluoroalkyl, —C(O)R$^9$, —CO$_2$R$^{10}$ or —C(O)NR$^7$R$^8$. More preferably, $R^1$ is —CF$_3$, —NO$_2$, —CN, —S(O)$_m$NR$^7$R$^8$, or —CO$_2$R$^{10}$, with —NO$_2$ being the most preferred. The $R^2$ group is preferably hydrogen, lower alkyl, —O-alkyl, —S-alkyl, aryl, arylalkyl, —O-aryl or —S-aryl. More preferably, $R^2$ will be methyl, ethyl, n-propyl, isopropyl, methoxy, ethoxy, propoxy, methoxymethyl, methylthio, ethylthio or propylthio.

In another group of preferred embodiments, $R^1$ is an electron-donating group and $R^2$ is an electron-withdrawing group. Within this group of embodiments, $R^1$ is preferably hydrogen, lower alkyl, —O-alkyl, —S-alkyl, aryl, arylalkyl, —O-aryl or —S-aryl. More preferably, $R^1$ is methyl, ethyl, n-propyl, isopropyl, methoxy, ethoxy, propoxy, methylthio, ethylthio or propylthio. The $R^2$ group is preferably —NO$_2$, —S(O)$_m$NR$^7$R$^8$, —S(O)$_n$R$^9$, —CN, halogen, fluoroalkyl, —C(O)R$^9$, —CO$_2$R$^{10}$ or —C(O)NR$^7$R$^8$. More preferably, $R^2$ is —CF$_3$, —NO$_2$, —CN, —S(O)$_m$NR$^7$R$^8$ or —CO$_2$R$^{10}$, with —NO$_2$ being the most preferred.

The groups $R^3$ and $R^4$ are independently hydrogen, alkyl, aryl or arylalkyl, or, taken together with the nitrogen atom to which each is attached form, a 5-, 6- or 7-membered ring containing from one to three heteroatoms in the ring. In one group of preferred embodiments, $R^3$ and $R^4$ are combined with the nitrogen atom to which each is attached, to form a 5- or 6-membered ring. The rings defined by $R^3$ and $R^4$ and the nitrogen atom can be saturated, unsaturated or aromatic, and can contain additional heteroatoms. Examples of suitable rings include: pyrrolidine, pyrrole, pyrazole, imidazole, imidazoline, thiazoline, piperidine, morpholine, and the like. In certain preferred embodiments, $R^3$ and $R^4$ are combined with the nitrogen atom to which each is attached to form a 5-membered ring containing two nitrogen atoms, preferably an imidazole ring, and most preferably a 2-alkylimidazole ring or a 5-alkylimidazole ring. Particularly preferred X groups are 2-methylimidazol-1yl, 2,4-dimethylimidazol-1yl, 2-ethylimidazol-1yl, 2-propylimidazol-1yl, 2-isopropylimidazol-1yl and 5-methylimidazol-1yl.

The $R^5$ group is an alkyl, aryl, arylalkyl or bicyclic fused aryl-cycloalkyl group. Preferred alkyl groups are those having from one to eight carbon atoms, either substituted or unsubstituted. Preferred aryl groups include substituted or unsubstituted phenyl, pyridyl, or naphthyl. Preferred arylalkyl groups include substituted and unsubstituted benzyl, phenethyl, pyridylmethyl and pyridylethyl. Particularly preferred $R^5$ groups are phenyl, 4-halophenyl, benzyl, n-butyl, propionyl, acetyl and methyl. Other preferred $R^5$ groups are those in which $R^5$ is combined with $R^6$ and the nitrogen atom to which each is attached to form a ring. Still other preferred $R^5$ groups (including some of the preferred fused bicyclic aryl-cycloalkyl groups) are selected from:

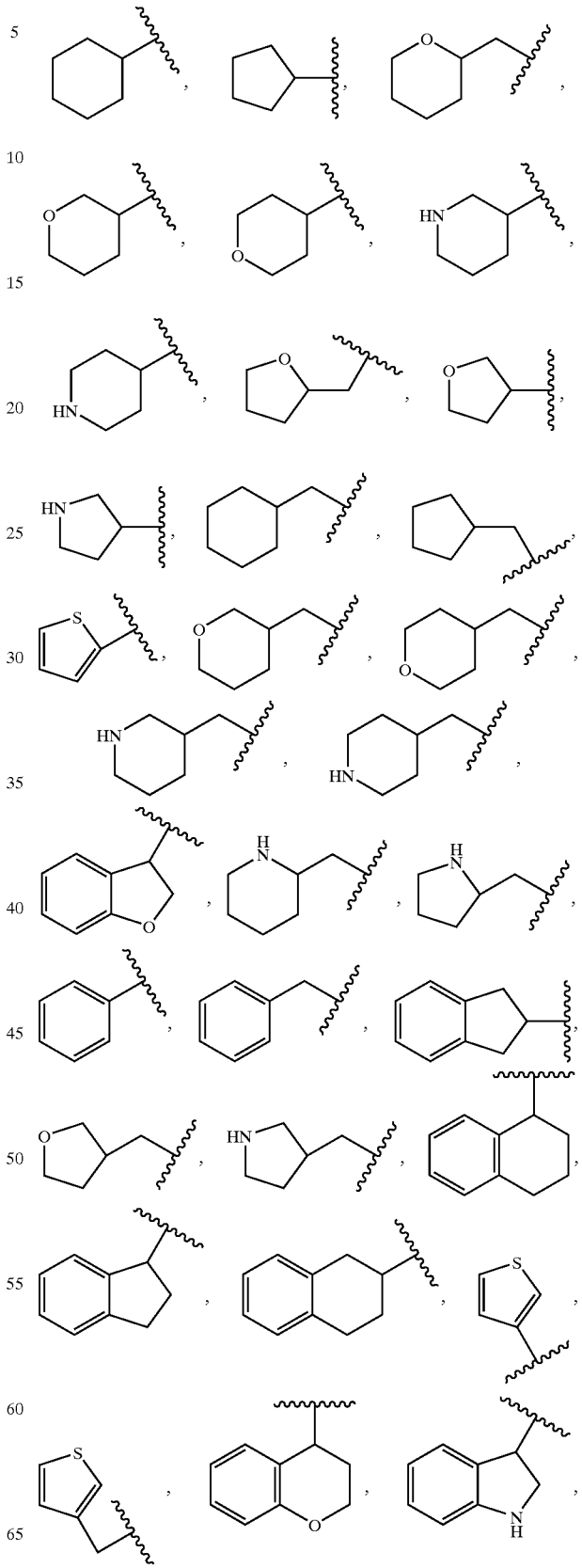

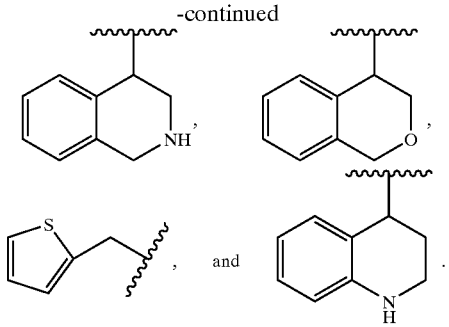

In the above radicals, and other groups described herein, the wavy line is used to indicate the point of attachment to the remainder of the molecule.

In one group of particularly preferred embodiments, $R^5$ is a radical selected from the group consisting of:

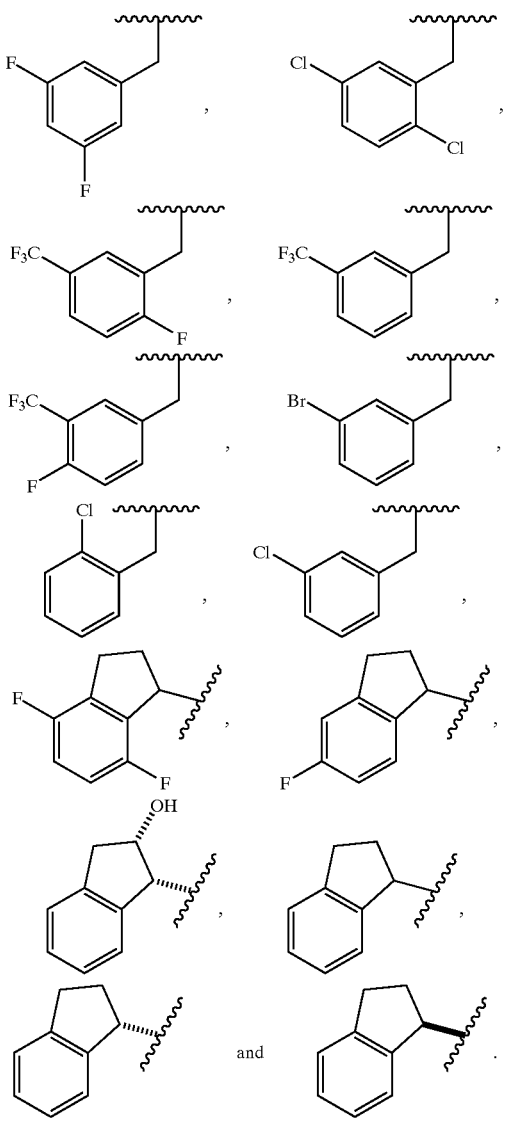

In another group of particularly preferred embodiments, $R^5$ is a radical selected from the group consisting of:

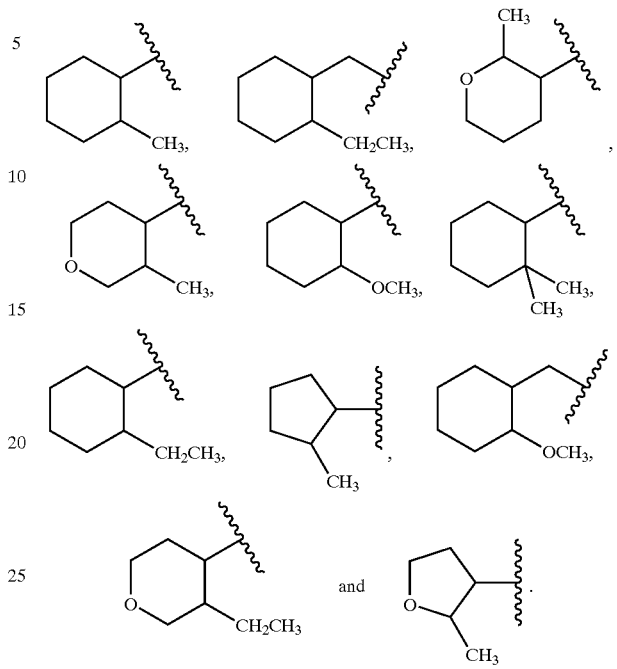

The above group of radicals is meant to include those radicals having a mixture of stereochemistry as well as pure isomers and enantiomers (those having less than about 5% of another diastereomer or enantiomer, more preferably less than about 2% of another isomer, and most preferably less than about 1% of another isomer).

The $R^6$ group is typically hydrogen, alkyl, aryl or arylalkyl. Preferably, $R^6$ is hydrogen, a lower alkyl group having from one to three carbon atoms, a phenyl ring or a phenylalkyl group, such as, for example, a benzyl or a phenethyl group. $R^7$ and $R^8$ are each independently hydrogen, alkyl, aryl or arylalkyl, or, taken together with the nitrogen atom to which each is attached, form a 4-, 5-, 6-, 7- or 8-membered ring containing from one to three heteroatoms in the ring. Preferably, $R^7$ and $R^8$ are each independently a (C1–C8) alkyl group, or are combined to form a 5-, 6-, or 7-membered ring. $R^9$ and $R^{10}$ are independently selected from hydrogen, alkyl, aryl and arylalkyl. In preferred embodiments, $R^9$ and $R^{10}$ are independently selected from hydrogen, (C1–C8) alkyl, phenyl and phenyl(C1–C4)alkyl. $R^{11}$ is alkyl, aryl or arylalkyl, preferably, (C1–C8)alkyl, phenyl and phenyl (C1–C4)alkyl.

In addition to the above descriptions of $R^1$ to $R^{11}$, the present formula above is meant to represent a number of compounds in which a second ring is fused to the pyrimidine ring, including structures in which one of the pyrimidine ring nitrogen atoms is at the ring junction. For the discussion below and the claims, the nitrogens are individually referred to as follows: $N^1$ is the nitrogen atom at the 1-position of the ring (which is between the carbon atom bearing —$R^2$ and the carbon atom bearing —Y—$R^5$). $N^3$ is the nitrogen atom at the 3-position of the pyrimidine ring (which is the nitrogen atom between the carbon bearing —Y—$R^5$ and the carbon atom bearing —X). Examples of fused rings are those in which $R^1$ is joined to $R^2$, $R^1$ is joined to $R^3$, $R^3$ is joined to $N^3$, $R^5$ is joined to $N^3$, $R^5$ is joined to $N^1$ or $R^2$ is joined to $N^1$ to form a fused 5-, 6-, or 7-membered ring. The ring formed by these combinations will contain 1–3 heteroatoms (e.g., O, N or S) and can be either aromatic or nonaromatic. Preferably the additional ring formed is a 5- or 6-membered ring.

When $R^1$ and $R^2$ are combined to form a ring, the combination can be replaced with a substituent of the formula —T—C(O)—(CH$_2$)$_s$—U—, wherein T and U are independently selected from —NH—, —O—, —CH$_2$— or a single bond, and the subscript s is an integer of from 0 to 2. Alternatively, the $R^1$ and $R^2$ radicals can be replaced with a substituent of the formula -A-(CH$_2$)$_p$—B—, wherein A and B are independently selected from —CH$_2$—, —O—, —NH—, —S—, —S(O)—, —S(O)$_2$—, —S(O)$_2$NR'— or a single bond, and p is an integer of from 1 to 3. One or more of the single bonds of the new ring so formed may optionally be replaced with a double bond. Alternatively, the $R^1$ and $R^2$ radicals can be replaced with a substituent of the formula —(CH$_2$)$_q$—Z—(CH$_2$)$_r$—, where q and r are independently integers of from 1 to 3, and Z is —O—, —NR'—, —S—, —S(O)—, —S(O)$_2$—, or —S(O)$_2$NR'—. The substituent R' in —NR'— and —S(O)$_2$NR'— is selected from hydrogen or (C1–C6)alkyl.

The subscript m, in the groups above, is an integer of from 1 to 2, preferably 2. The subscript n, in the groups above, is an integer of from 1 to 3, preferably 2.

Finally, the compounds of the present invention typically have a molecular weight of from about 150 to about 750. The compounds provided in the above formula are meant to include all pharmaceutically acceptable salts thereof.

A number of substituent combinations on the pyrimidine ring are particularly preferred. For example, one group of preferred embodiments has the formula:

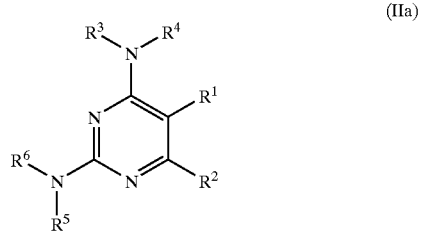

(IIa)

In compounds of general formula IIa, $R^1$ is preferably —NO$_2$, —CF$_3$, —C(O)NR$^7$R$^8$, —CO$_2$R$^{10}$, —S(O)$_2$NR$^7$R$^8$, —S(O)$_2$R$^9$, —C(O)R$^9$, —SO$_2$NH$_2$, or —CN and $R^2$ is preferably an alkyl group having from 1 to 8 carbon atoms. In the most preferred embodiments, the $R^3$ and $R^4$ groups are combined to form a 5-membered ring which is optionally fused to an aryl group. Examples of suitable 5-membered ring groups (and those which are optionally fused to an aryl group) include pyrrolidine, pyrrole, imidazole, pyrazole, benzimidazole, imidazoline, 1,2,4-triazole, 1,2,3-triazole, imidazolidin-2-one, and the like. More preferably, the $R^3$ and $R^4$ groups are combined to form an imidazole ring which is substituted or, optionally, is fused to an aryl group. Preferred substituted (and fused) imidazole rings include, for example, 2-methylimidazole, 2-ethylimidazole, 2-isopropylimidazole, 2-aminoimidazole, 5-methylimidazole, 5-ethylimidazole, 5-isopropylimidazole, 2,5-dimethylimidazole, benzimidazole, and 2-methylbenzimidazole. The $R^5$ and $R^6$ groups are independently selected from hydrogen, alkyl, aryl and arylalkyl, or can be combined with the nitrogen atom to which each is attached to form a ring which is optionally fused to an aryl group. FIG. 1 provides exemplary structures of compounds within this preferred group of embodiments.

Another group of preferred embodiments are represented by the formula:

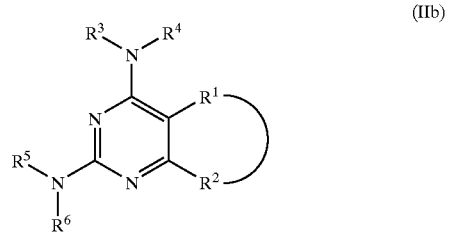

(IIb)

Figure 2:
FIG. 2 provides the structures of exemplary compounds of formula IIb.
Figure 2:
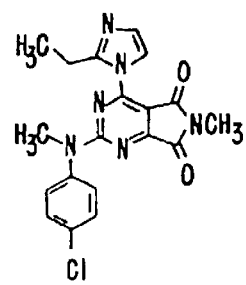
Figure 2:
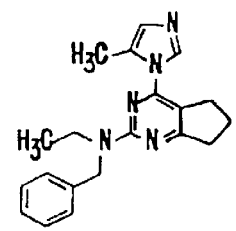
Figure 2:
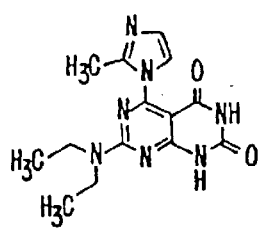
Figure 2:
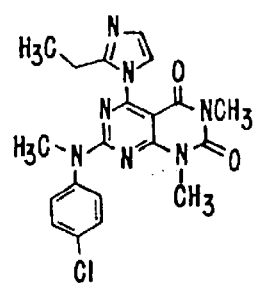
Figure 2:
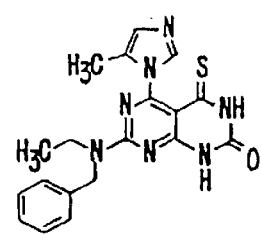
Figure 2:
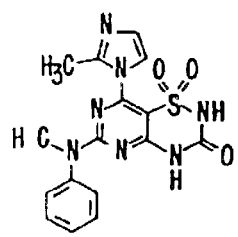
Figure 2:
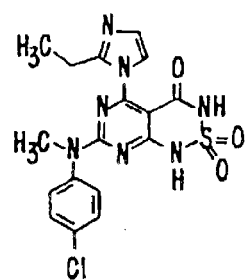
Figure 2:
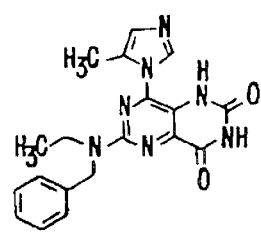

In this formula, the fused ring containing $R^1$ and $R^2$ is typically a heterocyclic ring in which the —R$^1$—R$^2$— group is selected from, for example, —S(O)$_2$NR'C(O)—, —S(O), NR'C(O)NR"—, —NR'S(O)$_2$NR"C(O)—, —C(O)NR'C (O)—, —NR'C(O)NR"C(O)—, —NR'C(S)NR"C(O)—, —NR'C(S)NR"C(S)—, in which R' and R" are independently hydrogen or (C1–C8)alkyl. The $R^3$ and $R^4$ groups are preferably combined to form a 5-membered ring which is optionally fused to an aryl group. More preferably, the $R^3$ and $R^4$ groups are combined to form an imidazole ring which is optionally fused to an aryl group. The $R^5$ and $R^6$ groups are independently selected from hydrogen, alkyl, aryl and arylalkyl, or can be combined to form a ring which is optionally fused to an aryl group. FIG. 2 provides exemplary structures of compounds within this preferred group of embodiments.

Yet another group of preferred embodiments is represented by the formula:

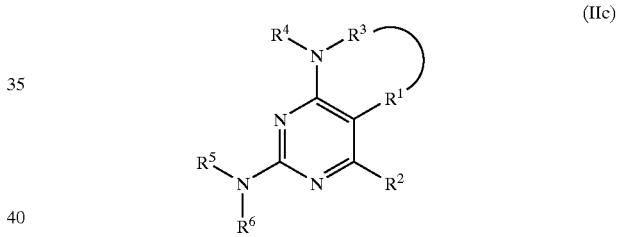

(IIc)

Figure 3:
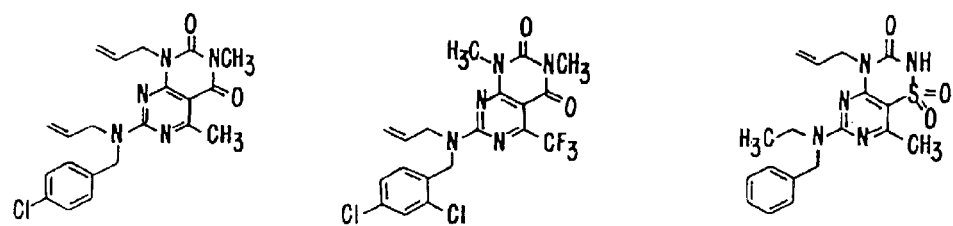
FIG. 3 provides the structures of exemplary compounds of formula IIc.

In this formula, the divalent radical —R$^1$—R$^3$— is typically an alkylene group, —C(O)NR'C(O)—, —C(O)NR'S (O)$_2$— or —S(O)$_2$NR'C(O)—, in which R' is a hydrogen or lower alkyl group. Preferably, $R^2$ and $R^4$ will each independently be an alkyl group, more preferably a lower alkyl group. The $R^5$ and $R^6$ groups are independently selected from hydrogen, alkyl, aryl and arylalkyl, or can be combined to form a ring which is optionally fused to an aryl group. FIG. 3 provides exemplary structures of compounds within this preferred group of embodiments.

Still another group of preferred embodiments are represented by the formula:

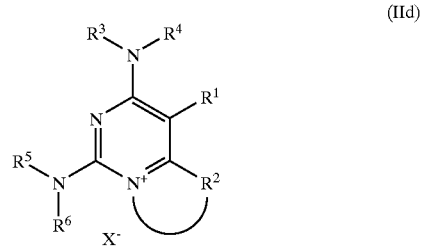

(IId)

Figure 4:
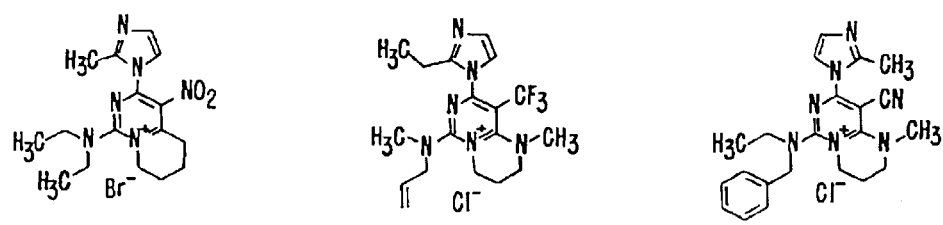
FIG. 4 provides the structures of exemplary compounds of formula IId.

In this formula, the fused ring portion defined by —R$^2$— is typically a (C3–C5)alkylene group, alkyleneamine group (e.g., —NHCH$_2$CH$_2$CH$_2$—, —NHCH$_2$CH$_2$—), or a —NR'C(O)CH$_2$— group, in which R' is hydrogen or a lower alkyl group. R$^1$ is typically —NO$_2$, —S(O)$_2$NR$^7$R$^8$, —S(O)$_2$R$^9$, —CN, —CF$_3$, —C(O)R$^9$, —CO$_2$R$^{10}$ or —C(O)NR$^7$R$^8$. More preferably, R$^1$ is —NO$_2$, —CN, —CF$_3$ or —CO$_2$R$^{10}$, with —NO$_2$ being the most preferred. The R$^3$ and R$^4$ groups are preferably combined to form a 5-membered ring which is optionally fused to an aryl group. More preferably, the R$^3$ and R$^4$ groups are combined to form an imidazole ring which is optionally fused to an aryl group. The R$^5$ and R$^6$ groups are independently selected from hydrogen, alkyl, aryl and arylalkyl, or can be combined to form a ring which is optionally fused to an aryl group. The symbol X$^-$ represents a suitable counterion for the quaternary nitrogen. Preferred counterions are those which form pharmaceutically acceptable salts. FIG. 4 provides exemplary structures of compounds within this preferred group of embodiments.

Another group of preferred embodiments are represented by the formula:

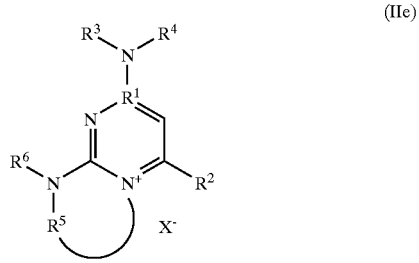

(IIe)

Figure 5:
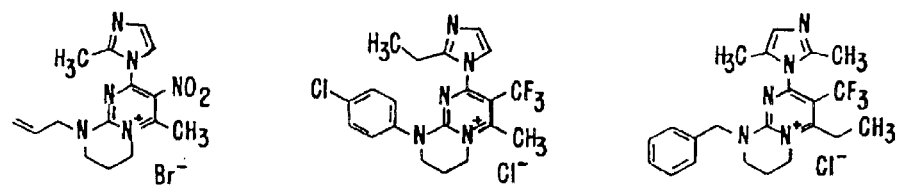
FIG. 5 provides the structures of exemplary compounds of formula IIe.

In this formula, R$^1$ is preferably —NO$_2$, —S(O)$_2$NR$^7$R$^8$, —S(O)$_2$R$^9$, —CN, —CF$_3$, —C(O)R$^9$, —CO$_2$R$^{10}$ or —C(O)NR$^7$R$^8$. More preferably, R$^1$ is —NO$_2$, —CN, —CF$_3$ or —CO$_2$R$^{10}$, with —NO$_2$ being the most preferred. R$^2$ is preferably an alkyl group having from 1 to 8 carbon atoms. The R$^3$ and R$^4$ groups are preferably combined to form a 5-membered ring which is optionally fused to an aryl group. More preferably, the R$^3$ and R$^4$ groups are combined to form an imidazole ring which is optionally fused to an aryl group. R$^6$ is preferably, (C1–C8)alkyl, phenyl, or phenylalkyl. The fused ring portion defined by —R$^5$— is typically a (C3–C5) alkylene group or a substituted alkylene group (e.g., —C(O)CH$_2$CH$_2$CH$_2$—, —C(O)CH$_2$CH$_2$—), or a —NR'C(O)CH$_2$— group, in which R' is hydrogen or a lower alkyl group. The symbol X$^-$ represents a suitable counterion for the quaternary nitrogen. Preferred counterions are those which form pharmaceutically acceptable salts. FIG. 5 provides the structures of exemplary compounds of formula IIe.

Compositions

In another aspect, the invention provides compositions which are suitable for pharmaceutical or diagnostic use. The compositions comprise compounds of formula I provided above, in combination with a diagnostically or pharmaceutically acceptable carrier or excipient.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a pro-drug, which can be metabolically or chemically converted to the subject compound by the recipient host. A wide variety of pro-drug derivatives are known in the art such as those that rely on hydrolytic cleavage or oxidative activation of the prodrug.

The compositions may be provided in any convenient form, including tablets, capsules, lozenges, troches, hard candies, powders, sprays, creams, suppositories, etc. As such, the compositions, in pharmaceutically acceptable dosage units or in bulk, may be incorporated into a wide variety of containers. For example, dosage units may be included in a variety of containers including capsules, pills, etc.

The compositions may be advantageously combined and/or used in combination with other antiviral agents which are either therapeutic or prophylactic agents, and different from the subject compounds. The compositions may also be advantageously combined and/or used in combination with agents that treat or induce conditions often associated with the viral infections that are sensitive to the present compounds, such as anti-HIV agents or immunosuppressive agents. In many instances, administration in conjunction with the subject compositions enhances the efficacy of such agents. Exemplary antiviral agents include ganciclovir, foscarnet and cidofovir. Exemplary anti-HIV agents include indinavir, ritonavir, AZT, lamivudine and saquinavir. Exemplary immunosuppressive agents include cyclosporin and FK-506. The compositions may also be advantageously used as antiviral prophylactic treatment in combination with immunosuppressive protocols such as bone-marrow destruction (either by radiation or chemotherapy).

Methods of Use

In yet another aspect, the present invention provides novel methods for the use of the foregoing compounds and compositions. In particular, the invention provides novel methods for treating or preventing viruses from the herpes family, preferably, cytomegalovirus infections. The methods typically involve administering to a patient an effective formulation of one or more of the subject compositions.

The invention provides methods of using the subject compounds and compositions to treat disease or provide medicinal prophylaxis to individuals who possess a compromised immune system or are expected to suffer immunosuppressed conditions, such as patients prior to undergoing immunosuppressive therapy in connection with organ transplantation or anticancer chemotherapy. These methods generally involve administering to the host an effective amount of the subject compounds or pharmaceutically acceptable compositions.

The compositions and compounds of the invention and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

Preparation of the Compounds

The compounds of the present invention can be prepared using general synthesis schemes such as those outlined in FIGS. 6–14. One of skill in the art will understand that the syntheses provided below can be modified to use different starting materials and alternate reagents to accomplish the desired transformations. Accordingly, the description below, the Figures and the reagents are all expressed as non-limiting embodiments.

Figure 6:
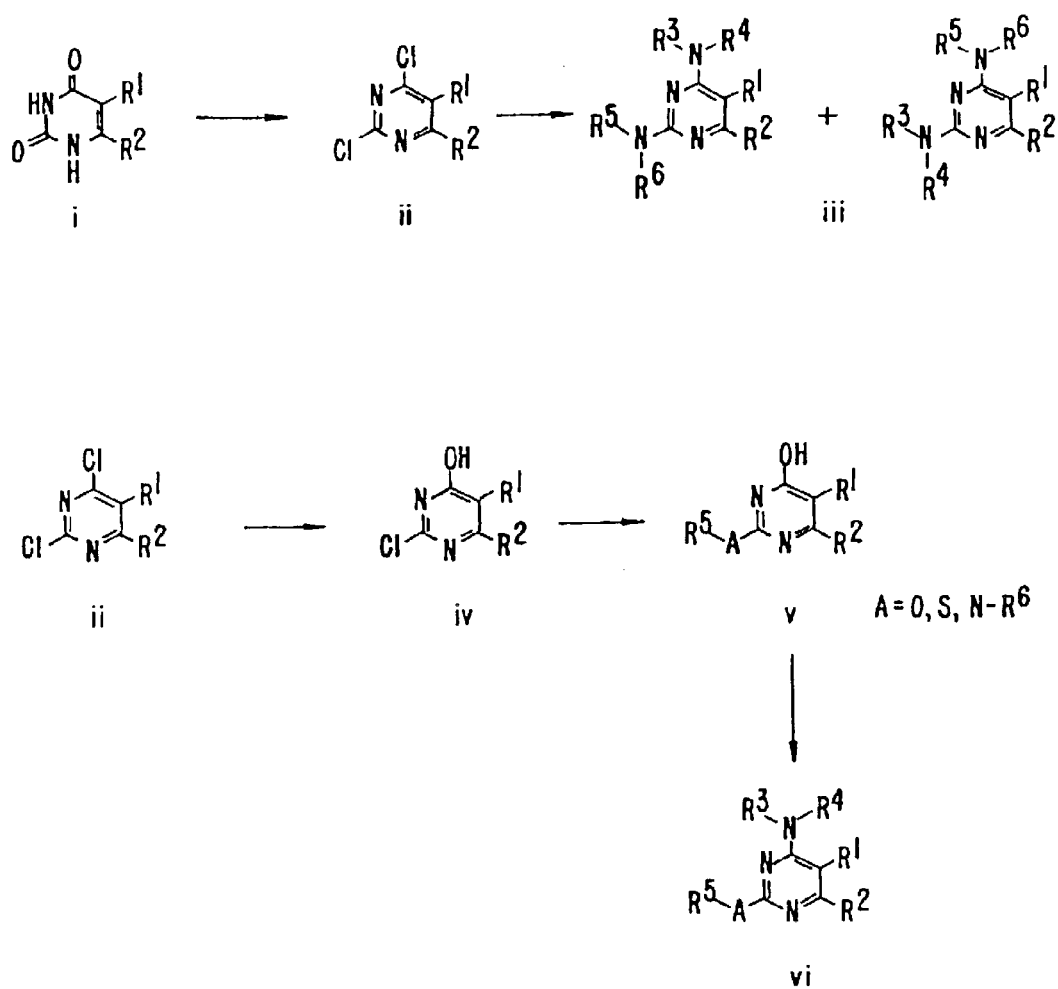
FIGS. 6–14 provide synthesis schemes for exemplary compounds of formulae IIa–IIe and also selected transformations for functional groups present on the compounds.

Briefly, the compounds of formula I, in which Y is —N(R$^6$)— can be prepared from a variety of known pyrimidinediones. As shown in FIG. 6, the pyrimidine dione (i) can be converted to the corresponding dichloride (ii) by treatment with reagents such as, for example, POCl$_3$. Treatment of ii with the desired amines (including heterocyclic amines) provides the target compounds, typically as a mixture of isomers (iii). Separation of the isomers can be accomplished by traditional methods such as column chromatography or HPLC. Alternatively, ii can be hydrolyzed to a mono chloro compound (using, for example, sodium acetate, acetic acid, water and ethanol) to provide (iv) which upon treatment with a suitable amine, alkoxide or thiolate ion provides (v). Conversion of the 4-hydroxy group to a 4-chloro substituent and displacement with a suitably nucleophilic amine provides the targets (vi).

Figure 7:
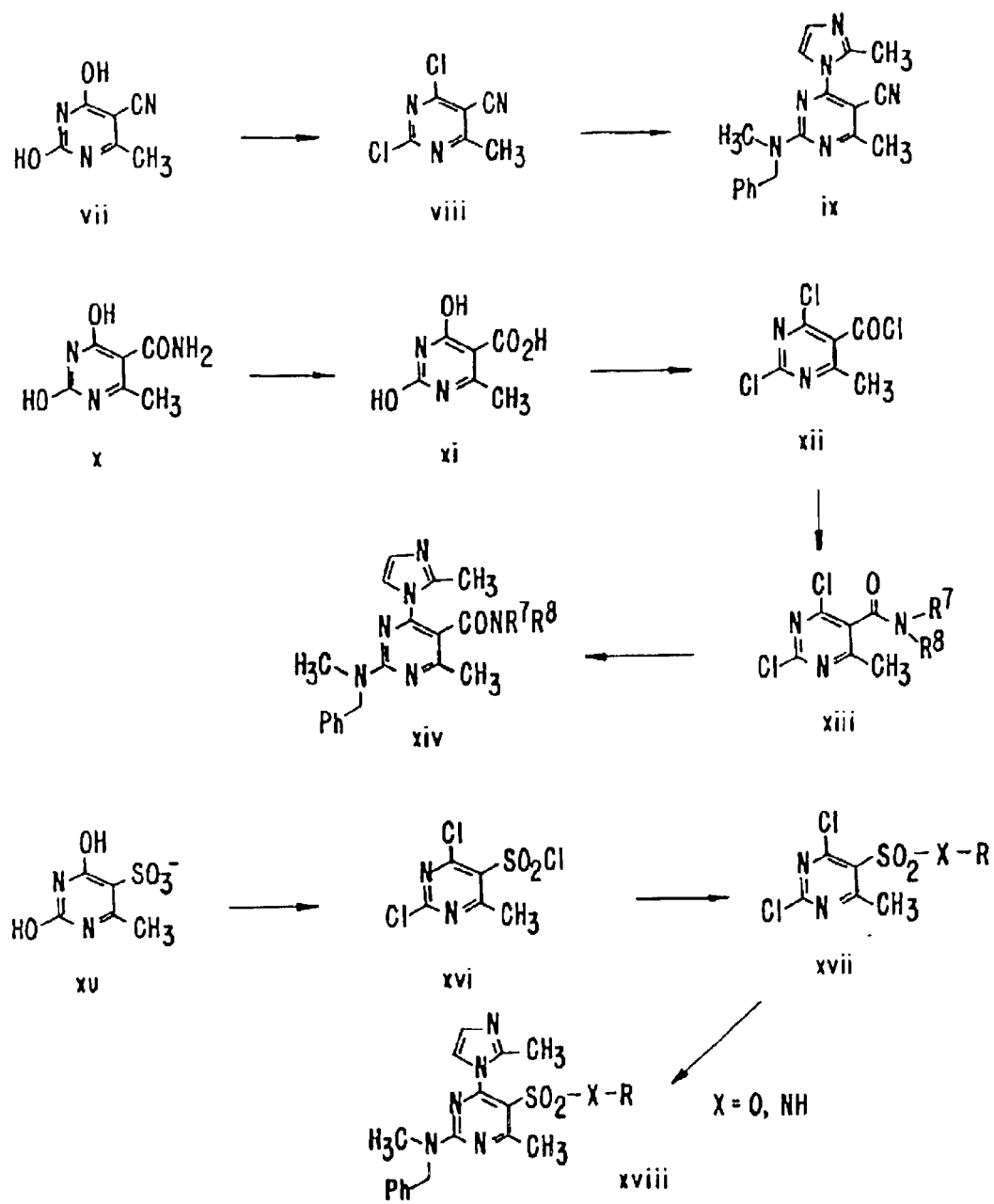

A number of pyrimidinediones are commercially available and can be used as starting materials for the above transformations, including, for example, 5-cyano-6-methyl-2,4-pyrimidinedione (vii), 6-methyl-2,4-pyrimidinedione-5-carboxamide (x), 6-methyl-2,4-pyrimidinedione-5-sulfonic acid (xv) and 6-methyl-5-nitro-2,4-pyrimidinedione. Each of these compounds can be converted to target compounds of formula (IIa) as illustrated in FIG. 7. For example, 5-cyano-6-methyl-2,4-pyrimidinedione (vii) can be converted to a dichloride (viii) using reagents such as POCl$_3$, then further converted to target compounds (e.g., ix) upon treatment with amines R$^3$—NH—R$^4$ (e.g., 2-methylimidazole) and R$^5$—NH—R$^6$ (N-methylbenzylamine).

The carboxamide group of 6-methyl-2,4-pyrimidinedione-5-carboxamide (x) can be hydrolyzed to a carboxylic acid (xi) with aqueous base and then converted to an acid chloride (xii) with POCl$_3$ (forming a trichloride). Stepwise addition of amines or other suitable nucleophiles provides the target compounds (e.g., xiv). Similarly, a trichloride (xvi) is formed by treating 6-methyl-2,4-pyrimidinedione-5-sulfonic acid (xv) with chlorinating agents such as POCl$_3$. Again, the stepwise addition of amines or other suitable nucleophiles produces the desired target species (xviii).

Figure 8:
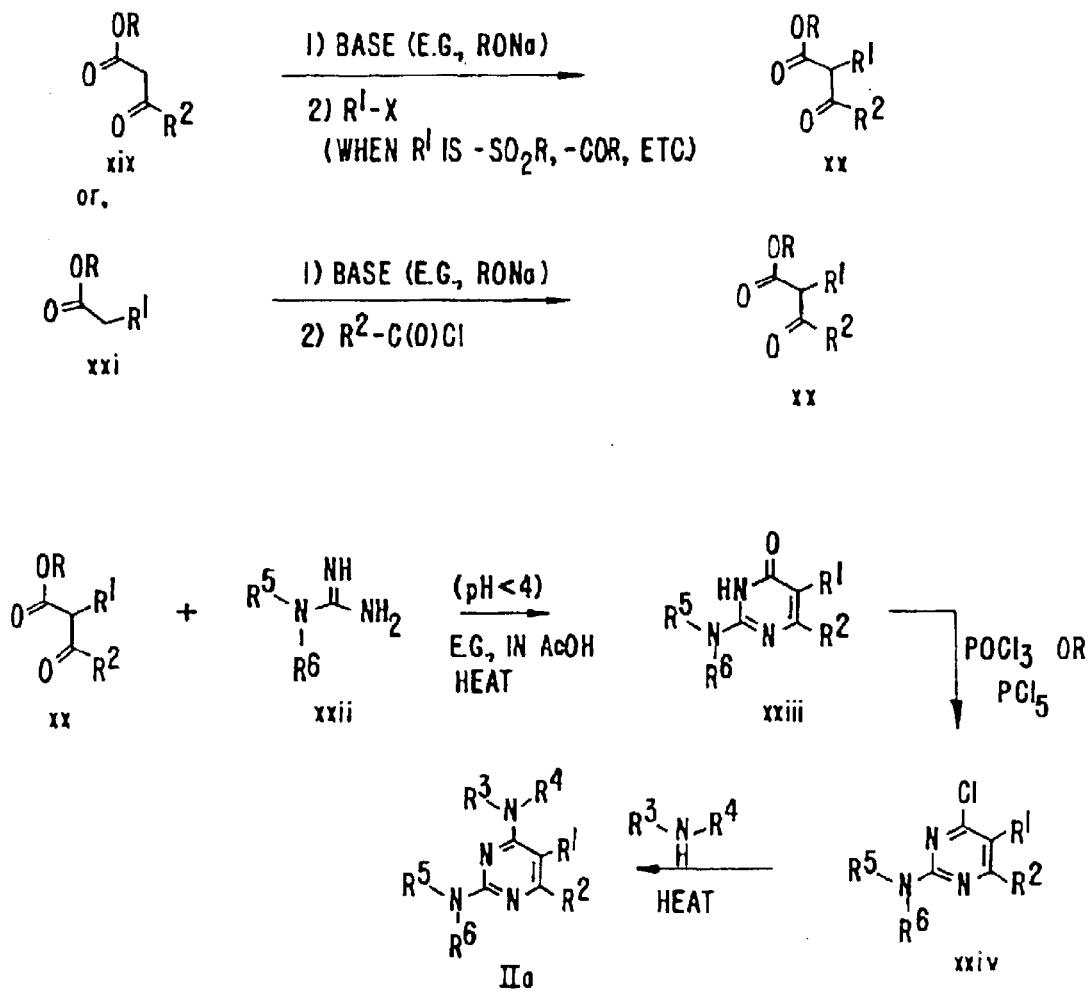
Figure 9A:
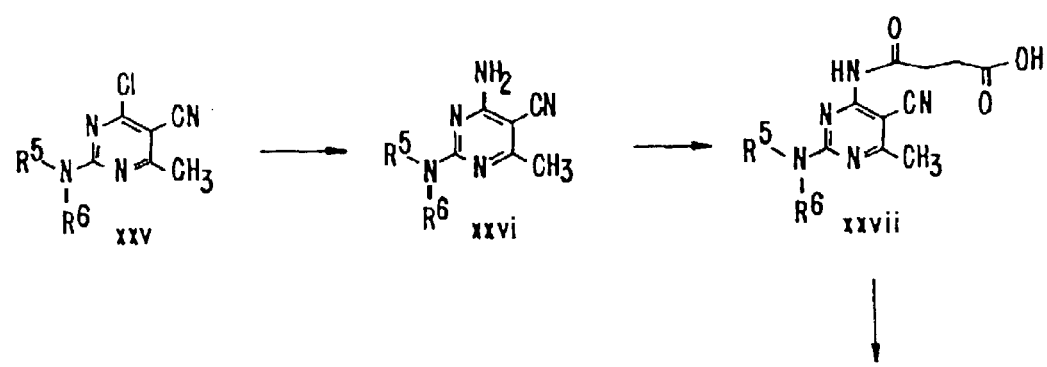
Figure 9B:
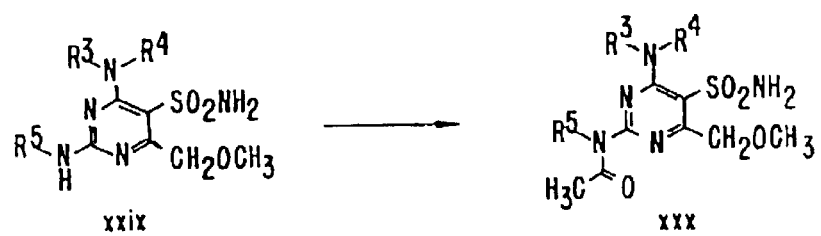
Figure 9C:
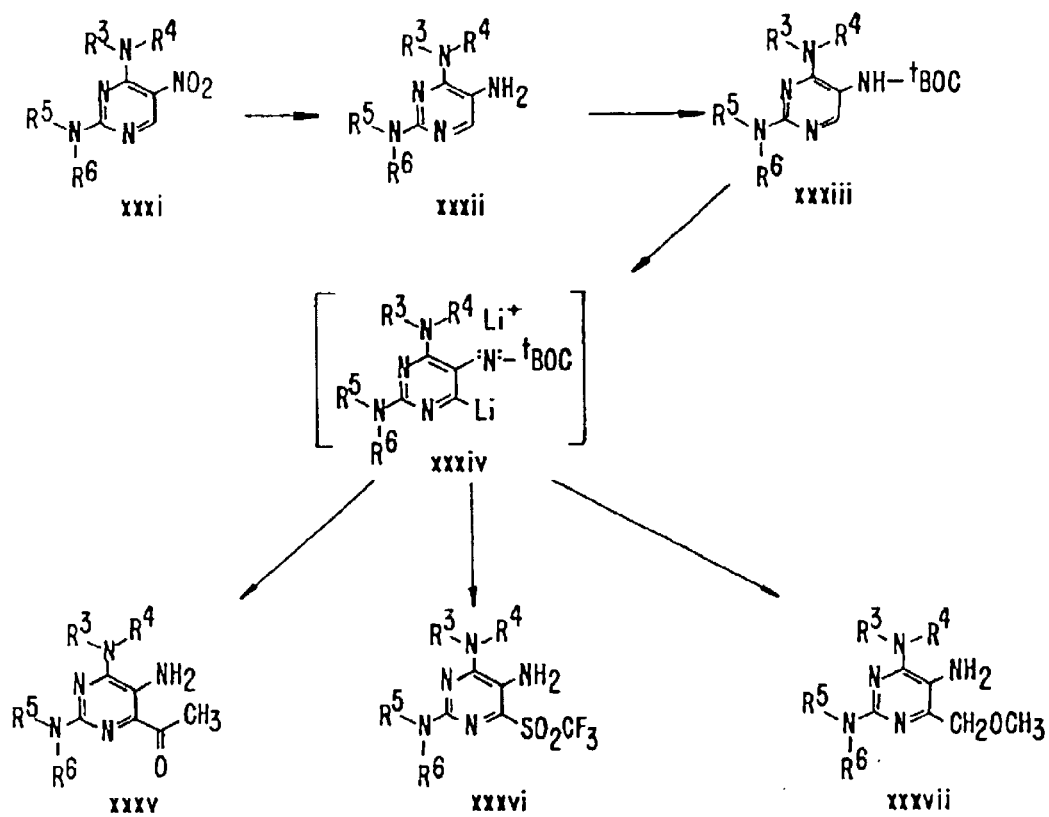
Figure 9D:
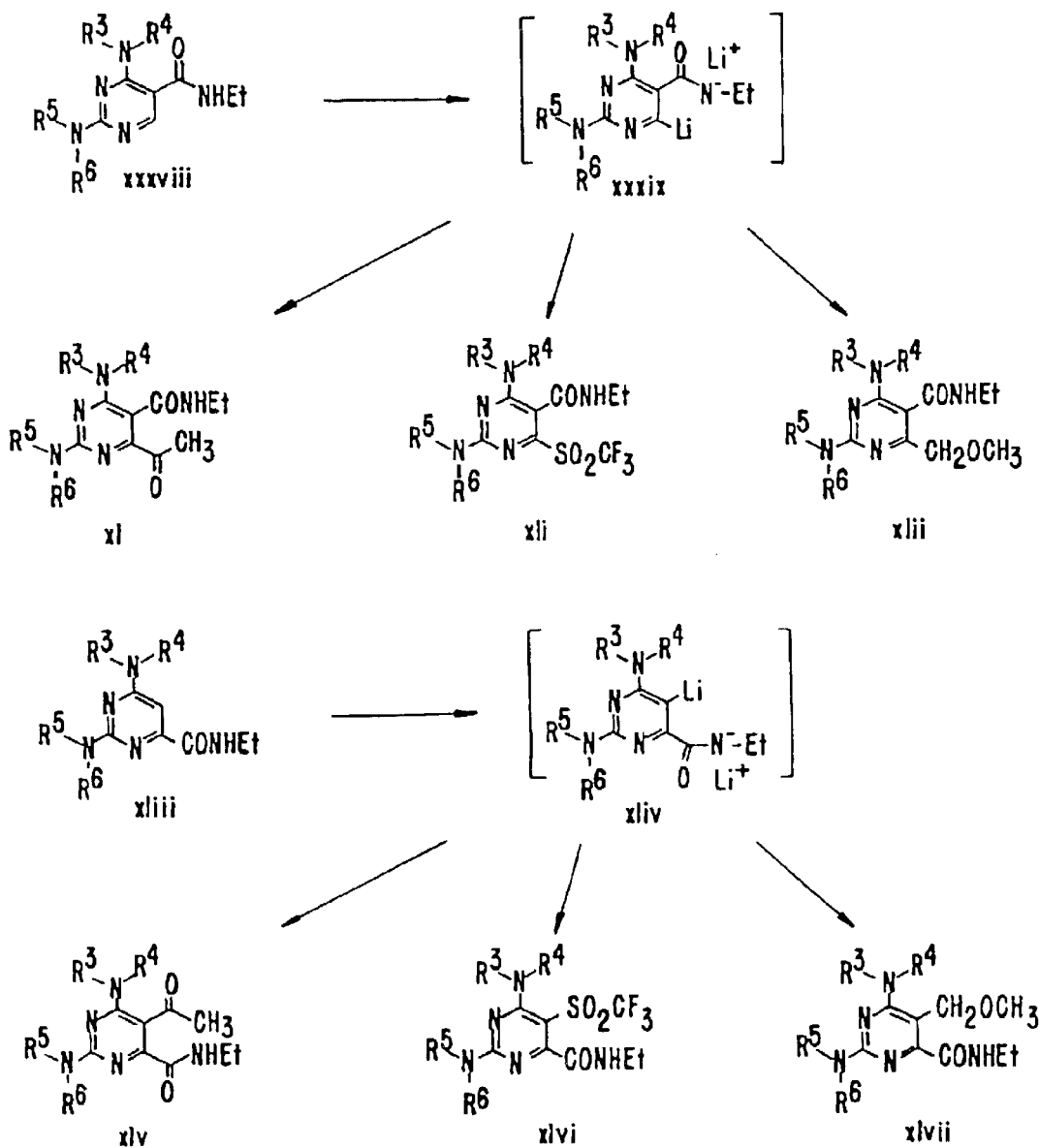

Yet another method for the preparation of compounds of formula IIa is shown in FIG. 8. Treatment of either a β-ketoester (xix) or an α-methylene ester (xxi) with base (e.g., sodium alkoxide) and an electrophile (e.g., an alkylating agent, acylating agent, sulfonylating agent, and the like) provides a suitably derivatized β-ketoester (xx) which can be converted to a pyrimidinone (xxiii) upon treatment with a substituted guanidine (xxii), typically in acid (acetic acid) with heating. The substituents in the 5- and 6-positions (R$^1$ and R$^2$, respectively) are determined by the groups present on the derivatized β-ketoester. Chlorination of the pyrimidinone to produce (xxiv) and subsequent treatment with a nucleophilic nitrogen heterocycle (e.g., imidazole, 2-alkylimidazole, pyrrolidine, piperidine and the like) as well as other amines provides the target compounds of formula IIa. Substituted guanidines used in this method of preparation can either be obtained from commercial sources or can be prepared by the treatment of a secondary amine with cyanamide. Additional literature methods for the preparation of substituted guanidines are known to those of skill in the art.

A number of transformations can be carried out to attach groups to an unsubstituted position on the pyrimidine ring, or to modify existing groups (see FIG. 9). For example, a 4-chloro substituent (present, for example, in xxv) can be displaced with ammonia to produce a 4-aminopyrimidine (e.g., xxvi). Treatment of the primary amine with succinic anhydride provides (xxvii) which upon treatment with acetic anhydride produces the succinimide compound xxviii (FIG. 9A). Exocyclic amino groups can also be acylated using standard acylating agents as shown in FIG. 9B. Metallation reactions can be carried out on pyrimidines which are unsubstituted in the 6-position (FIG. 9C). For example, a 5-nitropyrimidine derivative (xxxi) can be catalytically (H$_2$) or chemically (e.g., Fe/HCl) reduced to a 5-aminopyrimidine derivative (xxxii) which is then protected as a t-butyl carbamate (xxxiii). Treatment of the protected 5-aminopyrimidine derivative with a metallating agent such as sec-butyllithium provides a metallated intermediate (xxxiv) which can be acylated (xxxv), sulfonylated (xxxvi) or alkylated (xxxvii), as shown. Similarly (see FIG. 9D), the pyrimidine derivative (xxxviii) can be metallated to produce intermediate (xxxix), then acylated (xl), sulfonylated (xli) or alkylated (xlii). Introduction of functional groups at the 5-position can be accomplished using similar metallation chemistry on, for example, the pyrimidine derivative (xliii), to produce intermediate (xliv) which can be acylated (xlv), sulfonylated (xlvi) and alkylated (xlvii).

Figure 10A:
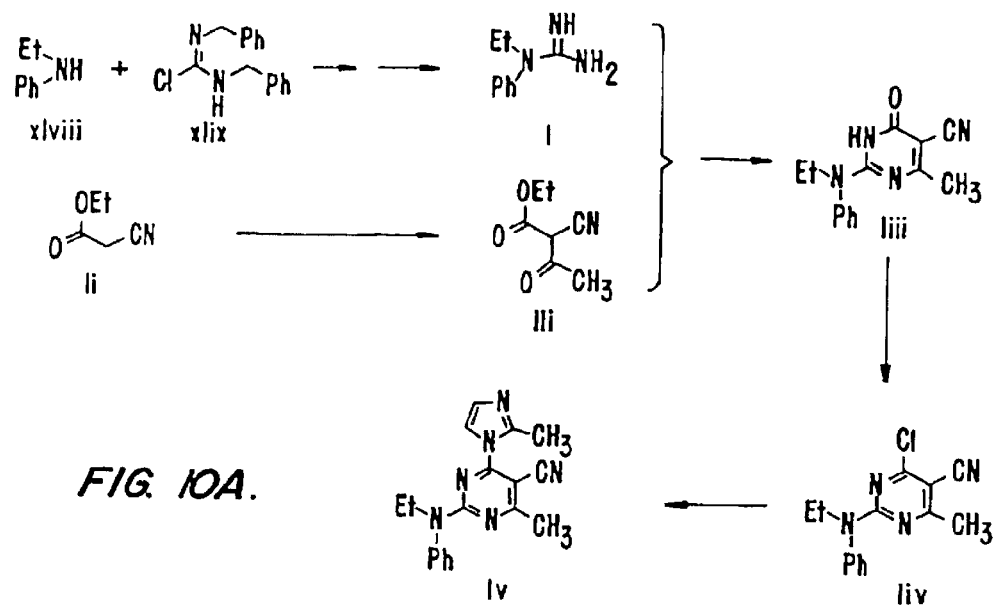
Figure 10B:
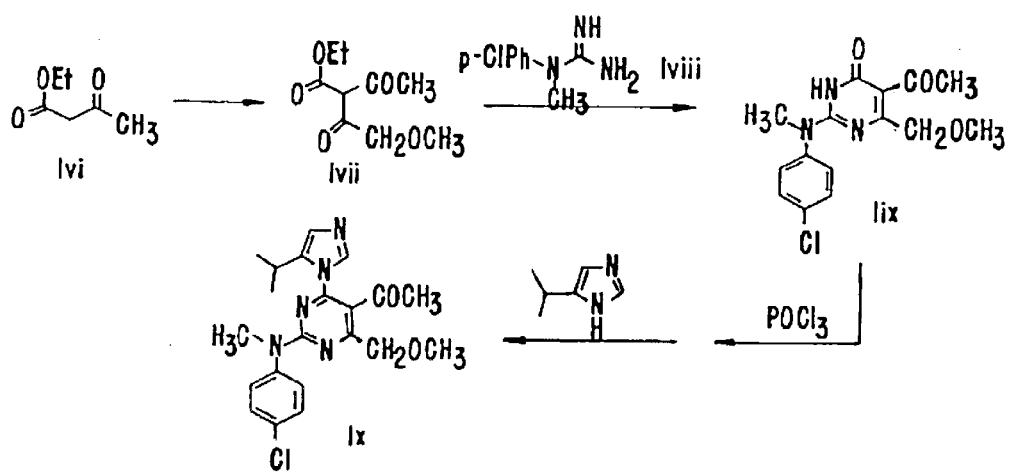
Figure 10C:
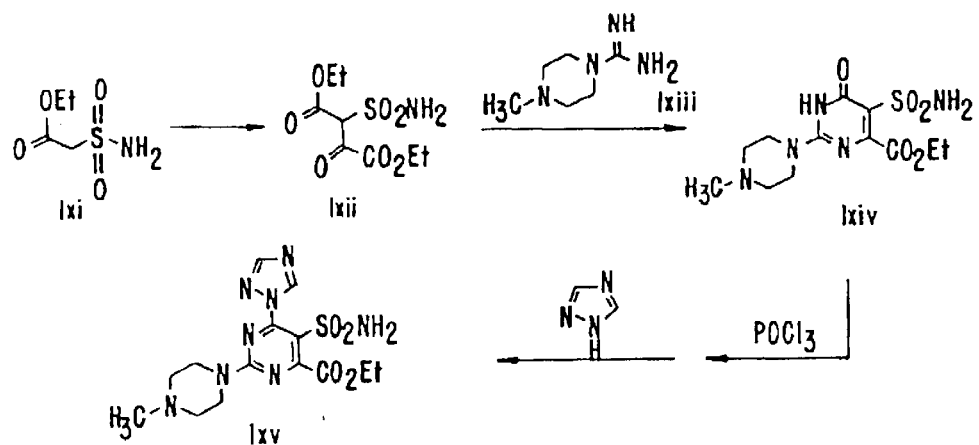
Figure 10D:
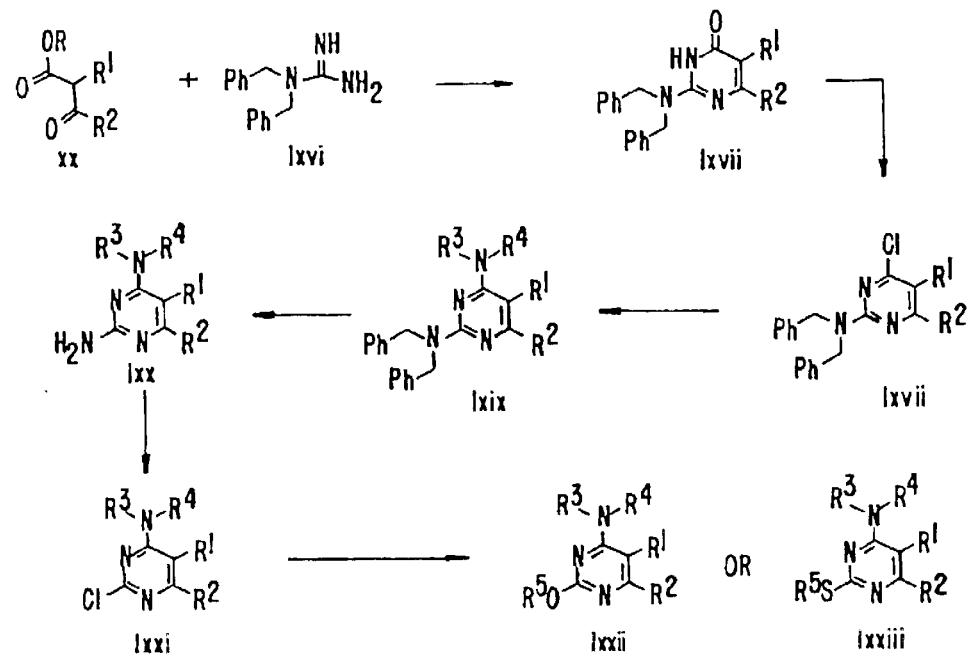

FIGS. 10A–10D provides synthesis schemes for several compounds which follow the general methods shown in FIGS. 6–8. For example, FIG. 10A illustrates the preparation of a substituted guanidine (l) from a secondary amine (xlviii) and a chloroimidate (xlix) and the conversion of ethyl cyanoacetate (li) to the ketoester (lii). Condensation of l and lii produces the pyrimidinone (liii) which can be chlorinated to provide liv and then treated with an amine nucleophile (e.g., 2-methylimidazole) to provide the target lv. FIG. 10B illustrates a similar route in which ethyl acetoactate (lvi) is acylated to provide the tricarbonyl compound (lvii). Condensation of lvii with the substituted guanidine (lviii) provides the pyrimidinone (lix) which is converted to the target (lx) using standard protocols. FIG. 10C illustrates methodology in which a sulfonamide group is present in the starting material (lxi) and the substituted guanidine (lxiii) contains a nitrogen heterocycle. Accordingly, condensation of lxii and lxiii provides the pyrimidinone (lxiv) which is converted to the target (lxv) using POCl$_3$ (or other chlorinating agents) followed by reaction with an amine nucleophile (e.g., 1,2,4-triazole). Additionally, the general methodology allows the preparation of compounds having —O—Ar, —S—Ar, —O-alkyl and —S-alkyl groups at the 2-position of the pyrimidine ring (FIG. 10D). For example, treatment of the ketoester (xx) with the substituted guanidine (lxvi) provides the pyrimidinone (lxvii) which can be chlorinated and condensed with R$^3$—NH—R$^4$ to provide lxix. Removal of the protecting groups yields the 2-aminopyrimidine compound (lxx). Diazotization and subsequent chlorination can be carried out using standard procedures to provide lxxi. Displacement of the chloride with either an oxygen-containing nucleophile or a sulfur-containing nucleophile provides the target compounds lxxii or lxxiii, respectively.

Figure 11A:
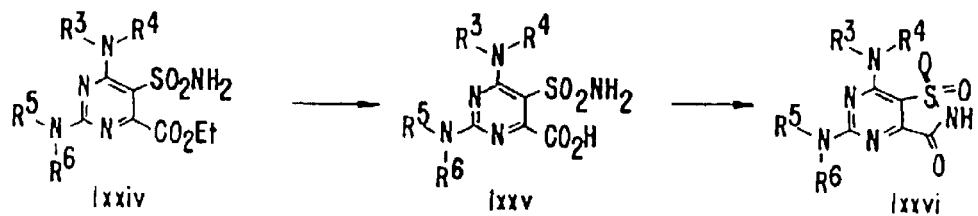
Figure 11B:
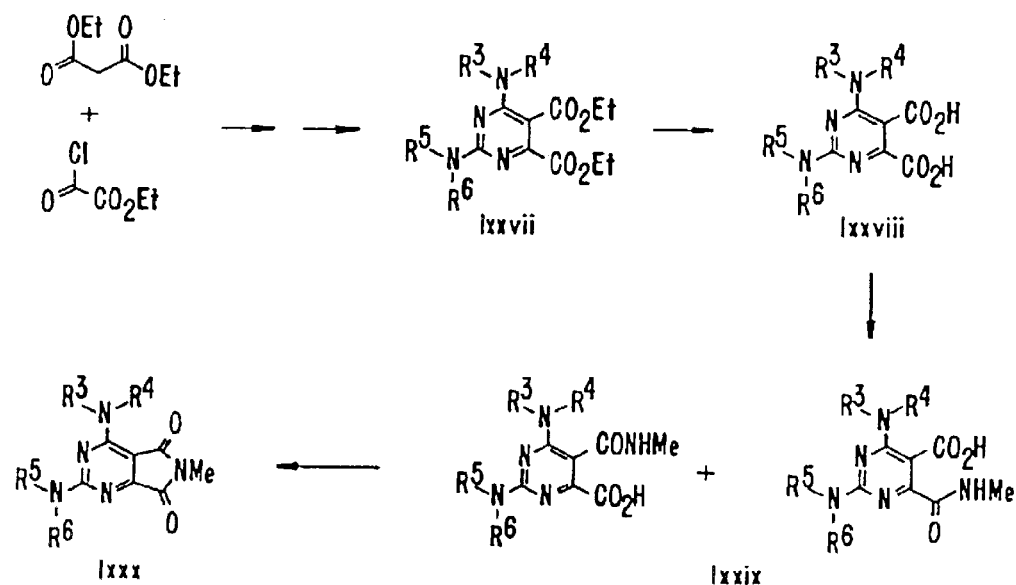
Figure 11G:
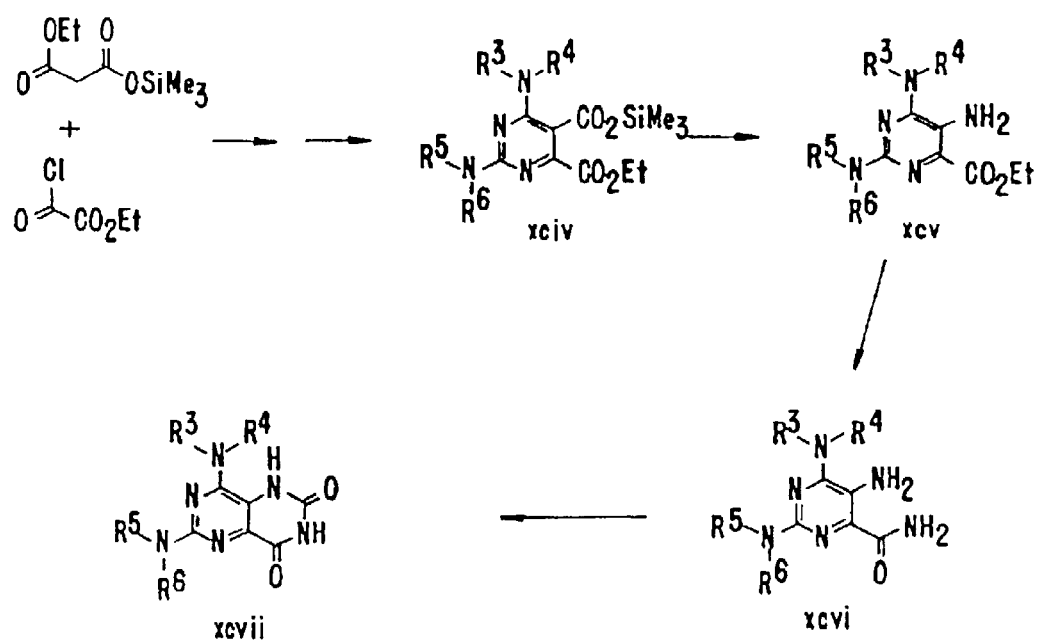

FIG. 11 illustrates the preparation of several compounds of formula IIb. In one group of embodiments, substituted pyrimidines having a sulfonamide at the 5-position and an ester group at the 6-position (lxxiv) can be saponified to provide lxxv, which is then cyclized with dehydrating agents (e.g., sulfuric acid or acetic anhydride) to the fused heterocycle shown as lxxvi (see FIG. 11A). In other embodiments, diesters (lxxvii) are saponified to the diacid (lxxviii) and converted to a mixture of amides (lxxix, by sequential treatment with acetic anhydride and methylamine), which can then be cyclized by treatment with a dehydrating agent (e.g., acetic anhydride) as indicated to provide a bicyclic system (lxxx, see FIG. 11B). Yet another fused bicyclic system (lxxxi) can be prepared beginning with ethyl 2-oxocyclopentanecarboxylate, using methods outlined above for the conversion of a β-ketoester to a substituted pyrimidine (see FIG. 11C). Still another group of embodiments can be prepared via manipulation of nitrile and ester substituents (see FIG. 11D). Briefly, ethyl cyanoacetate is first condensed with ethyl oxalyl chloride and the resultant product is treated with a substituted guanidine (exemplified herein with N,N-diethylguanidine) to provide the substituted pyrimidinone (lxxxii). Treatment of lxxxii with $POCl_3$ (or other chlorinating agent) followed by an appropriate amine (e.g., imidazole, 2-alkylimidazole, isopropylethylamine, pyrrolidine) provides the substituted pyrimidine (lxxxiii). Ester hydrolysis and Curtius rearrangement (using, for example, diphenylphosphoryl azide) provide the amino nitrile (lxxxiv). Conversion of the nitrile group to an amide by acid hydrolysis, and subsequent treatment with phosgene (or a phosgene equivalent such as diphosgene or dimethylcarbonate) provides the fused bicyclic system, lxxxv which can be further converted to lxxxvi on treatment with strong base (e.g., NaH) and an alkylating agent (e.g., MeI). Certain intermediates along these synthetic routes can be converted to other useful derivatives (FIG. 11E). For example, lxxxvii can be treated with Lawesson's reagent to provide the thioamide lxxxvii, which on treatment with phosgene (or a phosgene equivalent) provides the fused bicyclic system lxxxix. Alternatively, lxxxvii can be treated with sulfuryl chloride in the presence of a tertiary amine base to provide the fused bicyclic system xc. FIGS. 11F and 11G illustrate other methods of preparing compounds within the scope of formula IIb. In FIG. 11F, a substituted pyrimidine (xci) having a sulfonamide at the 5-position and a carboxylic acid at the 6-position is prepared using methods analogous to those described above. Curtius rearrangement of the carboxylic acid group in xci to an amino group provides. xcii, which is then cyclized to xciii, using phosgene or a phosgene equivalent. FIG. 11G shows the preparation of a pyrimidine diester (xciv) and its conversion to the fused bicyclic system xcvii. Briefly, the silyl ester present in xciv is hydrolyzed to the acid which is subjected to a Curtius rearrangement to provide xcv. Conversion of the remaining ester group to an amide can be accomplished using standard procedures to provide xcvi. Cyclization of xcvi to xcvii can be carried out using phosgene or a phosgene equivalent.

Figure 12A:
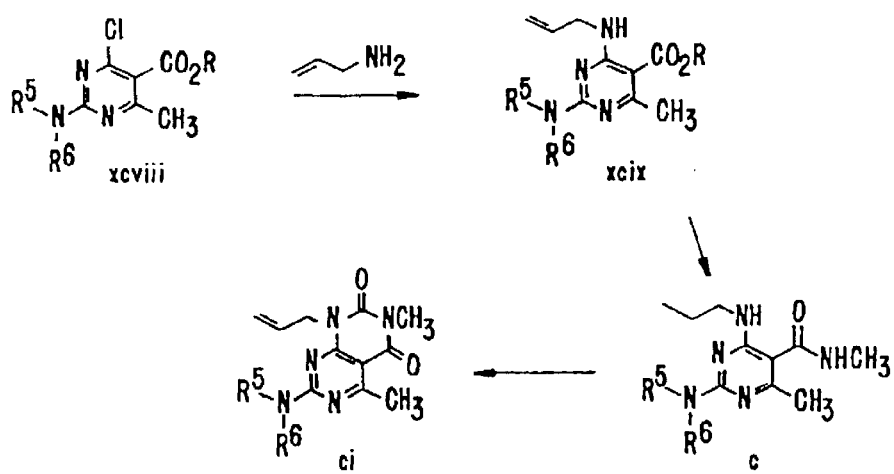
Figure 12B:
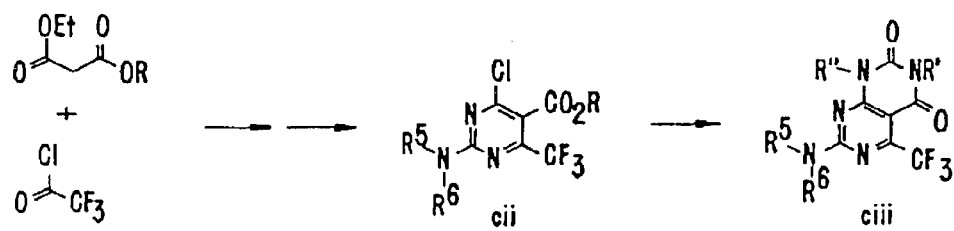
Figure 12C:
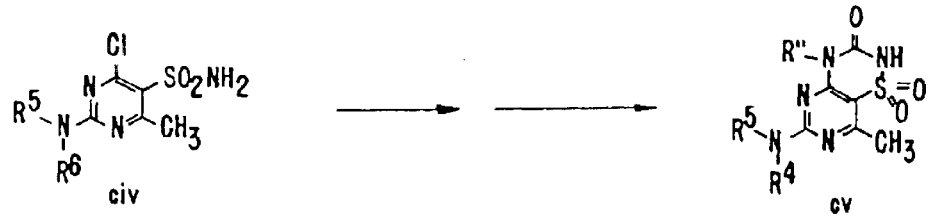

Compounds of formula IIc can be prepared by methods outlined in FIG. 12. In one group of embodiments (in FIG. 12A), a 4-chloropyrimidine derivative (xcviii, prepared by methods described above), is treated with an amine (e.g., allylamine) to provide xcix. The ester group is then converted to an N-methyl amide (c) upon treatment with methylamine in an alcohol solvent. Cyclization of c to ci occurs upon treatment with phosgene or an equivalent. Similarly, compounds having more electronegative groups in the 6-position can be prepared as shown in FIG. 12B. For example, the chloropyrimidine cii can be produced using methods outlined above and then converted to the bicyclic compound ciii, using procedures described for xcix. Still other fused systems of formula IIc can be prepared as shown in FIG. 12C. Here, a chloropyrimidine derivative (civ) is treated with a primary amine (e.g., allylamine) to provide an amino moiety at the 4-position of the pyrimidine ring. Cyclization of the amino moiety onto a sulfonamide (present at the 5-position) can be accomplished with phosgene or an equivalent to provide the target (cv).

Figure 13:
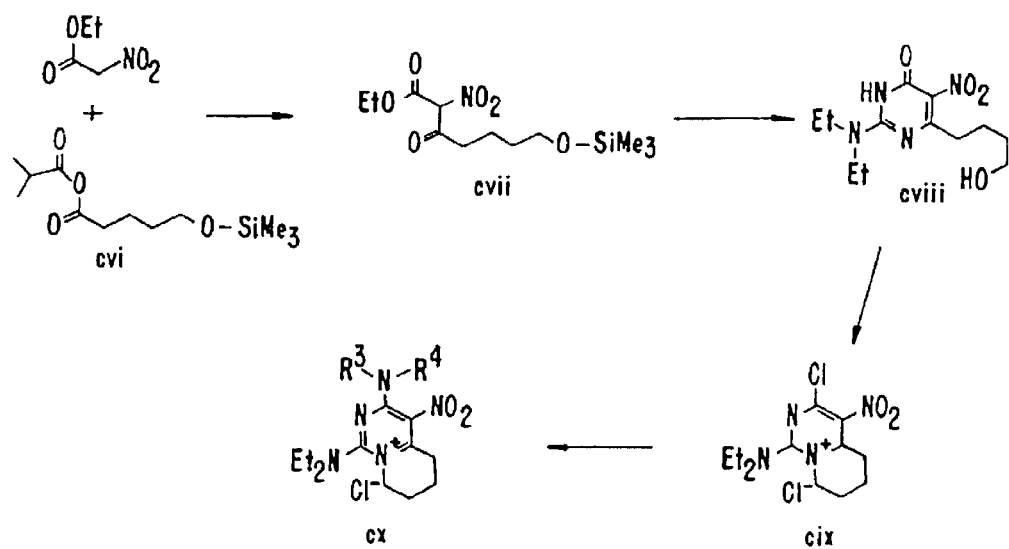

Preparation of compounds of formula IId can be accomplished, in one embodiment, as outlined in FIG. 13. Briefly, ethyl nitroacetate can be condensed with a mixed anhydride (cvi) to provide a nitroketoester (cvii) which can then be converted to a pyrimidine (cviii) upon treatment with a suitably substituted guanidine. Removal of the protecting group, followed by treatment with $POCl_3$ effects chlorination of the pyrimidine ring and cyclization to form a pyrimidinium salt (cix). Treatment of cix with an amine nucleophile produces the target compound (cx). Other compounds in this group can be prepared by starting with ethyl 3,3,3-trifluoropropionate or ethyl cyanoacetate and varying both the substituted guanidine and the amino nucleophile which are used.

Figure 14:
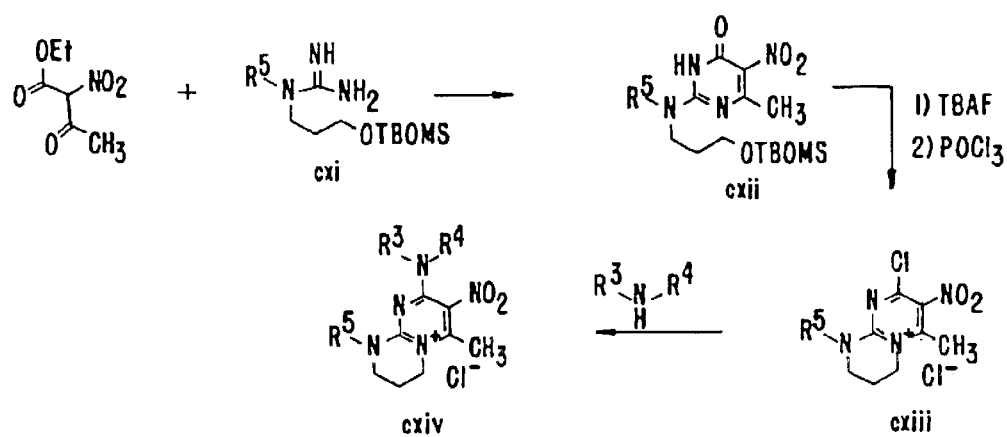

Preparation of certain compounds of formula IIe can be accomplished following procedures outlined in FIG. 14. According to the scheme depicted in FIG. 14, a suitably substituted guanidine (cxi, prepared from a protected hydroxypropylamine) is condensed with ethyl 2-nitroacetoacetate (or similarly ethyl 2-trifluoromethylacetoacetate) to provide the a pyrimidinone (cxii). Removal of the protecting group, chlorination and cyclization using procedures similar to those shown in FIG. 13, produces the salt (cxiii). Subsequent treatment of cxiii with a nucleophilic amine produces the target (cxiv).

The compounds used as initial starting materials in this invention may be purchased from commercial sources or alternatively are readily synthesized by standard procedures which are well know to those of ordinary skill in the art.

Some of the compounds of the present invention will exist as stereoisomers, and the invention includes all active stereoisomeric forms of these compounds. In the case of optically active isomers, such compounds may be obtained from corresponding optically active precursors using the procedures described above or by resolving racemic mixtures. The resolution may be carried out using various techniques such as chromatography with a chiral solid support or a chiral solvent, repeated recrystallization of derived asymmetric salts, or derivatization, which techniques are well known to those of ordinary skill in the art.

The compounds of the invention may be labeled in a variety of ways. For example, the compounds may contain radioactive isotopes such as, for example, $^3H$ (tritium), $^{125}I$ (iodine-125) and $^{14}C$ (carbon-14). Similarly, the compounds may be advantageously joined, covalently or noncovalently, directly or through a linker molecule, to a wide variety of other compounds, which may provide pro-drugs or function as carriers, labels, adjuvents, coactivators, stabilizers, etc. Such labeled and joined compounds are contemplated within the present invention.

Analysis of Compounds

The subject compounds and compositions were demonstrated to have pharmacological activity in in vitro and in vivo assays, e.g., they are capable of specifically modulating a cellular physiology to reduce an associated pathology or provide or enhance a prophylaxis.

Certain preferred compounds and compositions are capable of specifically inhibiting or suppressing cytomegalovirus infection. For the assessment of activity against human CMV, a method was used which is similar to that described in Kohler, et al., J. Virol. 68:6589–6597 (1994). Briefly, a recombinant human cytomegalovirus (HCMV) was made containing a marker gene (luciferase) under the control of the promoter for the late 28 kDa viral structural phosphoprotein pp28. Human foreskin fibroblast (HFF) cells were infected with the recombinant HCMV virus (MOI 5), placed into 96-well plates, and cultured under standard cell-culture conditions. Compounds that were evaluated for anti-HCMV activity were added to the infected cells 1 hour later. The level of luciferase expression was measured 24 hours after treatment with the test compounds. The biological activity of the test compounds is described by their IC$_{50}$ values, the concentration of test compound that reduces recombinant HCMV late gene expression (represented by luciferase expression in the HFF culture) by 50% relative to control (vehicle-treated) infected cells. As an additional control, the cytotoxicity of test compounds on untreated HFF cells was also evaluated in cultured cell growth experiments.

Table 1 provides biological data for selected compounds from the examples below.

TABLE 1

| Compound | IC$_{50}$ (μM) |
|---|---|
| a | 0.8 |
| c | 0.1 |
| d | 0.02 |
| f | 6.0 |
| g | 0.8 |
| h | 0.3 |
| j | 0.01 |
| k | 1.0 |
| m | 2.0 |
| n | 0.4 |
| o | 2.0 |
| p | 0.3 |
| q | 3.0 |
| s | 3.0 |
| t | 10.0 |
| u | 0.1 |

The following examples are offered by way of illustration and not by way of limitation.

EXAMPLES $^1$H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz. Electron Ionization (EI) mass spectra were recorded on a Hewlett Packard 5989A mass spectrometer. Mass spectrometry results are reported as the ratio of mass over charge, followed by the relative abundance of each ion (in parentheses). All reagents, starting materials and intermediates utilized in these examples are readily available from commercial sources or are readily prepared by methods known to those skilled in the art.

Example 1

This example illustrates the synthesis of 2-(N-methylanilino)-4-(2-methylimidazol-1-yl)-6-methyl-5-nitropyrimidine (a) and an isomer 4-(N-methylanilino)-2-(2-methylimidazol-1-yl)-6-methyl-5-nitropyrimidine (b).

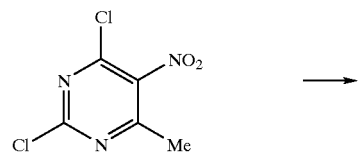

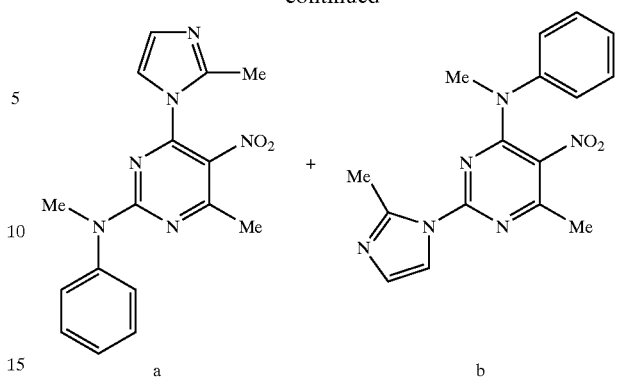

To a stirred cold (−78° C.) solution of 2,4-dichloro-6-methyl-5-nitropyrimidine (2.25 g, 10.8 mmol, 1.0 eq) in THF (15 mL) was added 2-methylimidazole (977 mg, 11.9 mmol, 1.1 eq) in a solution of THF (15 mL) dropwise. After 1 hour, the dry ice bath was replaced with a water ice bath and stirring was continued for an additional 2 hours and 15 minutes. At this time N-methylaniline (4.6 mL, 43.2 mmol, 4.0 eq) was added. The reaction solution was stirred 1 hour and 15 minutes at −78° C. and at room temperature overnight. At this time the solvent was removed and the residue was diluted with dichloromethane and washed three times with 0.1M HCl and three times with saturated aqueous NaCl solution. The organic phase was evaporated and the residue was purified by chromatography on silica gel (1:1 hexane/diethyl ether, 1% AcOH as eluant) to provide 209 mg of the target compound a (6%) along with an isomer (400 mg) and b (104.8 mg).

(a) $^1$H NMR (400 MHz) (CD$_3$OD): δ 2.26 (3H, br s); 2.58 (3H, br s); 3.61 (3H, s); 6.88 (1H, s); 7.02 (2H, d); 7.31–7.34 (3H, m); 7.43–7.48 (2H, m). Anal. calcd. for C$_{16}$H$_{16}$N$_6$O$_2$: C, 59.25; H, 4.97; N, 25.91. Found C, 59.16; H, 4.95; N, 25.86.

(b) $^1$H NMR (400 MHz) (CDCl$_3$): δ 2.40 (3H, s); 2.80 (3H, s); 3.55 (3H, s); 6.95 (1H, s); 7.13 (2H, m); 7.30–7.39 (3H, m); 7.86 (2H, s).

Example 2

This example illustrates the synthesis of 2-(N-methylanilino)-4-(2-methylimidazol-1-yl)-6-ethyl-5-nitropyrimidine (c).

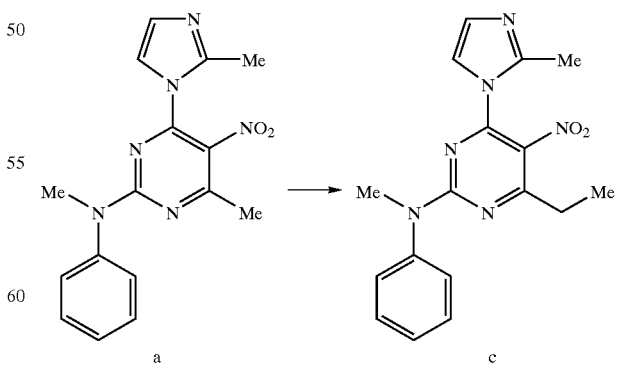

To a stirred, cold (−78° C.) solution of a (54.4 mg, 0.168 mmol, 1.0 eq) in THF (1.0 mL) was added LiN(SiMe$_3$)$_2$, (0.20 mmol, 0.20 mL, of a 1.0 M/THF solution) dropwise.

After stirring for 10 minutes, MeI (0.105 mL, 1.68 mmol, 10 eq) was added dropwise. The reaction was kept at −78° C. for 40 minutes and stirred for an additional 4 hours at 0° C. A small portion of acetic acid (0.25 mL) was poured into the flask and the brown residue was evaporated to dryness. The residue was then dissolved in dichloromethane and washed three times with saturated aqueous NaCl solution and the organic phase was evaporated to dryness to provide a crude yellow oil.

Purification was carried out by column chromatography on silica gel with 1:1 hexane/diethyl ether, 1% AcOH, 3% MeOH as eluant, to provide 21.4 mg of the desired product (37%).

(c) $^1$H NMR (400 MHz) (CD$_3$OD): δ 1.29 (3H, br s); 2.28 (3H, br s); 2.86 (2H, br s); 3.63 (3H, s); 6.89 (1H, s); 7.02 (1H, s); 7.30–7.39 (3H, m); 7.42–7.49 (2H, m).

MS ESI m/z (relative intensity): M+H, 339.2 (100); M+Na, 361.1 (15).

Example 3

This example illustrates the synthesis of 2-(N-benzyl-N-methylamino)-4-(2-methylimidazol-1-yl)-6-methyl-5-nitropyrimidine (d), 2,4-bis-(N-benzyl-N-methylamino)-6-methyl-5-nitropyrimidine (e) and 4-(N-benzyl-N-methylamino)-2-(2-methylimidazol-1-yl)-6-methyl-5-nitropyrimidine (f).

N-methylbenzylamine (0.465 mL, 3.6 mmol, 4.0 eq) was added. After stirring for 2.7 hours, the solvents were removed by evaporation. The residue was diluted with dichloromethane and washed three times with 0.1M HCl and three times with saturated aqueous NaCl solution. Solvent was removed from the organic phase and the residue was purified by chromatography on silica gel (1:1 hexane/diethyl ether, 1% AcOH, as eluant) to provide d (32 mg), e (116.3 mg) and f (104.8 mg).

(d) $^1$H NMR (400 MHz) (CDCl$_3$): δ 2.30 (1.5 H, s); 2.53 (1.5 H, s); 2.57 (1.5 H, s); 2.59 (1.5 H, s); 3.15 (1.5 H, s); 3.27 (1.5 H, s); 4.88 (1H, s); 4.97 (1H, s); 6.87 (0.5 H, s); 6.90 (0.5 H, s); 6.96 (0.5 H, s); 6.99 (0.5 H, s); 7.16 (1H, d); 7.24–7.37 (4H, m).

MS ESI m/z (relative intensity): M+H, 339.2 (100); M+Na, 361.1 (8)

(e) $^1$H NMR (400 MHz) (CDCl$_3$): δ 2.49 (3H, s); 2.79 (3H, s); 2.90–3.20 (3H, br m); 4.70–4.88 (4H, br m); 7.12–7.35 (10H, br m). MS ESI m/z (relative intensity): M+H, 378.2 (100); M+Na, 400.1 (15)

(f) $^1$H NMR (400 MHz) (CDCl$_3$): δ 2.52 (3H, s); 2.67 (3H, s); 2.90 (3H, s); 4.92 (2H, s); 6.89 (1H, s); 7.20 (2H, d); 7.28–7.35 (3H, m); 7.74 (1H, s). MS ESI m/z (relative intensity): M+H, 339.2 (100).

Example 4

This example illustrates the synthesis of of 2-(N-methyl-4-chloroanilino)-4-(2-methylimidazol-1-yl)-6-methyl-5-nitropyrimidine (g).

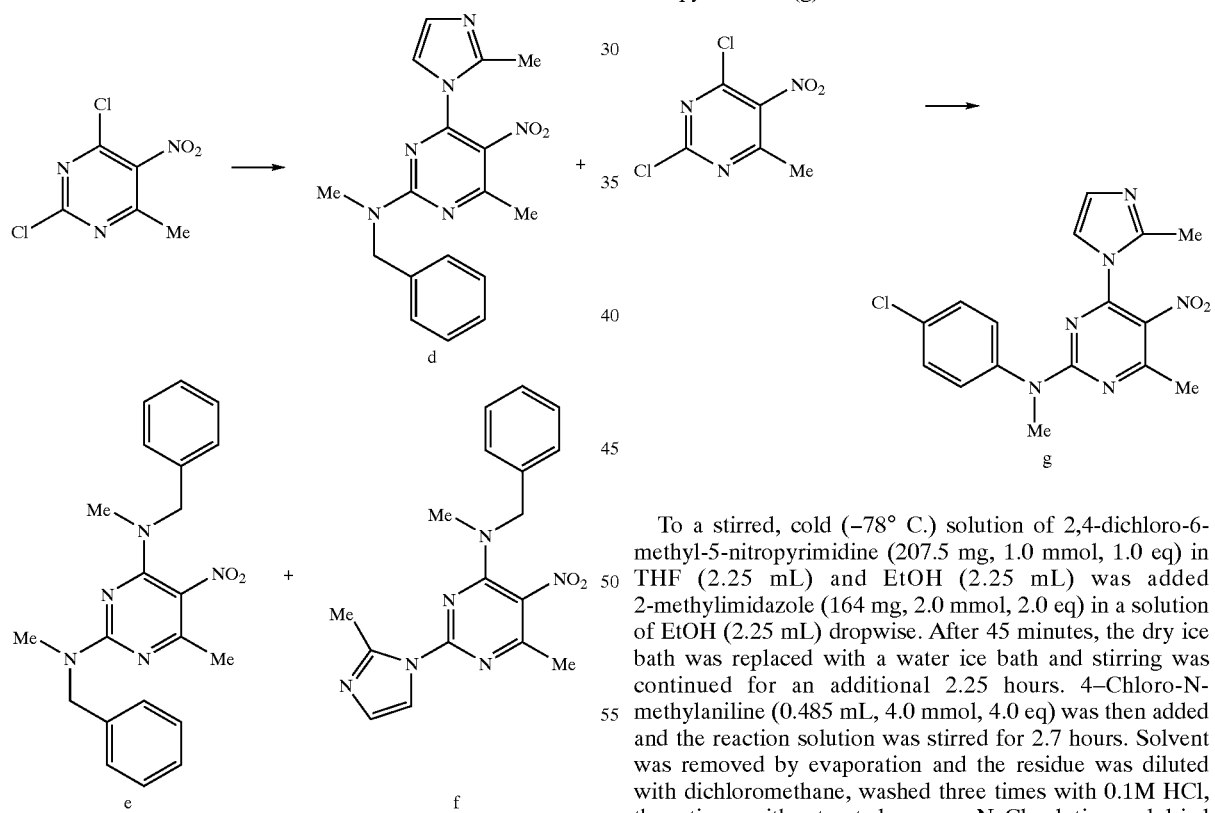

To a stirred, cold (−78° C.) solution of 2,4-dichloro-6-methyl-5-nitropyrimidine (207.5 mg, 1.0 mmol, 1.0 eq) in THF (2.25 mL) and EtOH (2.25 mL) was added 2-methylimidazole (164 mg, 2.0 mmol, 2.0 eq) in a solution of EtOH (2.25 mL) dropwise. After 45 minutes, the dry ice bath was replaced with a water ice bath and stirring was continued for an additional 2.25 hours. 4–Chloro-N-methylaniline (0.485 mL, 4.0 mmol, 4.0 eq) was then added and the reaction solution was stirred for 2.7 hours. Solvent was removed by evaporation and the residue was diluted with dichloromethane, washed three times with 0.1M HCl, three times with saturated aqueous NaCl solution and dried over MgSO$_4$. Solvent was removed from the organic phase and the residue was purified by silica gel chromatography (1:1 hexane/diethyl ether, 1% AcOH as eluant) to provide g (55.9 mg, 15.6%).

To a stirred, cold (−78° C.) solution of 2,4-dichloro-6-methyl-5-nitropyrimidine (187.7 mg, 0.9 mmol, 1.0 eq) in THF (2.25 mL) and EtOH (2.25 mL) was added 2-methylimidazole (148 mg, 1.8 mmol, 2.0 eq) in a solution of EtOH (2.25 mL) dropwise. After 45 minutes, the dry ice bath was replaced with a water ice bath and the mixture was stirred for an additional 2.2 hours. At this time (g) $^1$H NMR (400 MHz) (CD$_3$OD): δ 2.30 (3H, br s); 2.57 (3H, br s); 3.59 (3H, s); 6.91 (1H, s); 7.02 (1H, s); 7.36 (2H, d); 7.44 (2H,d). MS ESI m/z (relative intensity): M+H, 359.1 (100).

Example 5

This example illustrates the synthesis of 2-(N-methylanilino)-4-(2-methylimidazol-1-yl)-6-isopropyl-5-nitropyrimidine (h).

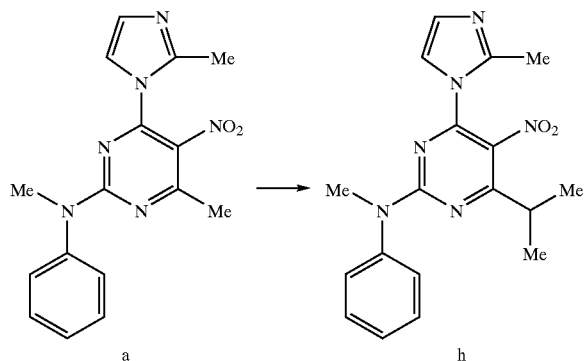

To a stirred, cold (−78° C.) solution of a (38.6 mg, 0.12 mmol, 1.0 eq) in THF (0.5 mL) was added NaH (9.5 mg, 60% in oil 0.24 mmol, 2.0 eq). After stirring for 15 minutes, MeI (0.074 mL, 1.19 mmol, 10 eq) was added. The reaction was kept at −78° C. for 2 hours, then stirred an additional 2.5 hours at 0° C. A small portion of acetic acid (0.25 mL) was poured into the flask and the brown mixture was evaporated to dryness. The residue was dissolved into dichloromethane, washed three times with water and three times with saturated aqueous NaCl solution. Solvent was removed from the organic phase and the product was purified by silica gel chromatography (1:1 hexane/diethyl ether, 1% AcOH as eluant) to provide the target compound (13.3 mg 33%).

(h) $^1$H NMR (400 MHz) (CDCl$_3$): δ 1.20–1.35 (6 H, m); 2.29 (3H, br s); 3.24 (1H, m); 3.62 (3H, s); 4.92 (2H, s); 6.89 (1H, br s); 7.03 (1H, br s); 7.30–7.40 (3H, m); 7.71–7.48 (2H, m). MS ESI m/z (relative intensity): M+H, 353.1 (100).

Example 6

This example illustrates the synthesis of 2-(N-benzyl-N-methylamino)-4-(2-methylimidazol-1-yl)-6-ethyl-5-nitropyrimidine (j).

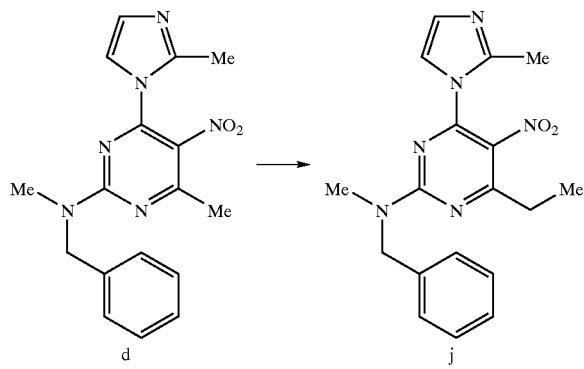

To a stirred, cold (−78° C.) solution of d (57.7 mg, 0.170 mmol in THF (0.5 mL) was added LiN(SiMe$_3$)$_2$, (0.17 mL, 0.17 mmol, 1.0 eq, 1.0 M/THF) dropwise. After stirring for 10 minutes, MeI (0.106 mL, 1.70 mmol, 10 eq) was added dropwise. The reaction was kept at −78° C. for 2 hours and then stirred for an additional 3 hours at 0° C. A small portion of acetic acid (0.25 mL) was poured into the flask and the brown mixture was evaporated to dryness. The residue was dissolved into dichloromethane, washed three times with water, three times with saturated aqueous NaCl solution and the organic phase was evaporated to dryness. The target compound was obtained following silica gel chromatography (1:1 hexane/diethyl ether, 1% AcOH, 3% MeOH as eluant). Yield: 30.3 mg (50.4%).

(j) $^1$H NMR (400 MHz) (CD$_3$OD): δ 1.26–1.41 (3H,m); 2.21 (1.5 H,s); 2.45 (1.5 H, s); 2.86–2.94 (2H, m); 3.22 (1.5 H, s); 3.35 (1.5 H, s); 4.93 (1H, s); 5.05 (1H,s); 6.91 (0.5 H, s); 6.94 (0.5 H, s); 7.07 (0.5 H, s); 7.12 (0.5 H, s); 7.23–7.38 (5 H, m). MS ESI m/z (relative intensity): M+H, 353.1 (100).

Example 7

This example illustrates the synthesis of 2-(N,N-diethylamino)-4-(2-methylimidazol-1-yl)-6-methyl-5-nitropyrimidine (k).

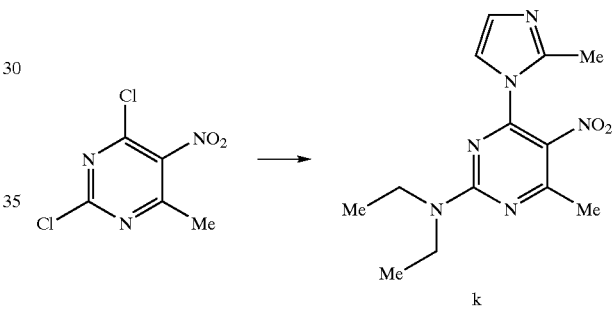

To a cooled (−78° C.) solution of 2,4-dichloro-6-methyl-5-nitropyrimidine (208 mg, 1.0 mmol, 1.0 eq. in 2 mL each of EtOH and THF) was added 2-methylimidazole (164 mg, 2.0 mmol, 2.0 eq.) in 2 mL of EtOH. The resulting mixture was stirred for 1 hour at −78° C., then for 2 hours at 0° C. Diethylamine (0.413 mL, 4.0 eq.) was added dropwise and the reaction was stirred overnight. The resulting mixture was diluted with dichloromethane, washed with 0.1N HCl, saturated NaCl, dried (MgSO$_4$), and filtered. Solvent was removed by evaporation and the residue was purified by silica gel chromatography to provide 35 mg of the target compound k as an oil.

(k) $^1$H NMR (400 MHz, CDCl$_3$): δ 1.15–1.23 (3H, m); 2.48 (3H, s); 2.53 (3H, s); 3.59–3.60 (2H, q); 3.68–3.70 (2H, q); 6.86 (1H, s); 6.95 (1H, s). MS ESI m/z (relative intensity): M+H, 291.2 (100).

In a similar manner, the following compounds were prepared using the indicated amine in place of diethylamine. Each was obtained as a yellow oil.

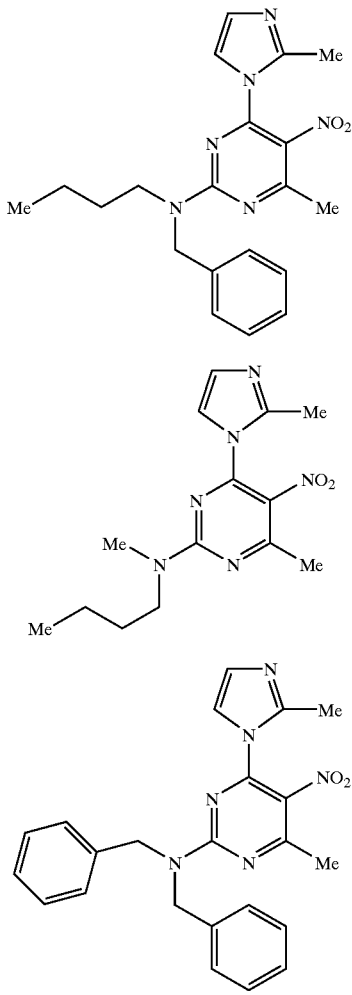

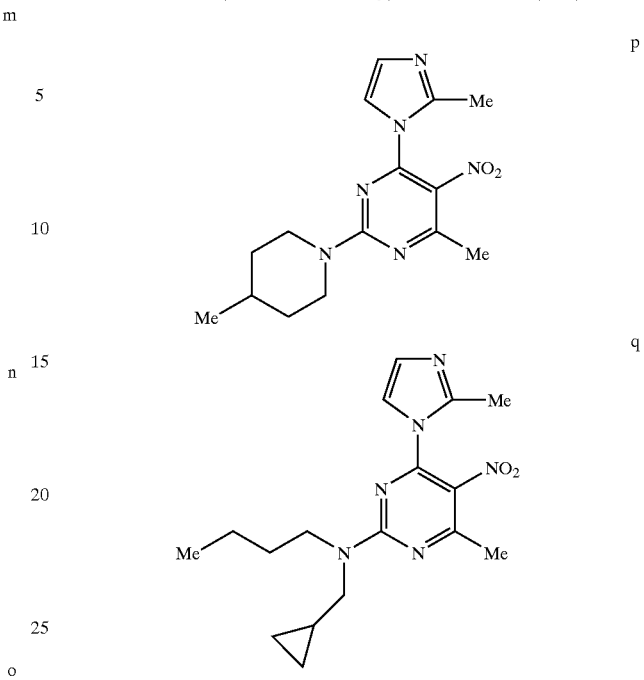

2-(N-benzylbutylamino)-4-(2-methylimidazol-1-yl)-6-methyl-5-nitropyrimidine Compound m (N-butylbenzylamine)—40 mg. ¹H NMR (400 MHz, CDCl₃): δ 0.86–0.95 (3H, m); 1.23–1.38 (2H, m); 1.51–1.68 (2H, m); 2.52 (3H, m); 3.52 (2H, t); 4.83 (1H, s); 6.80 (1H, s); 6.92 (1H, s); 7.13 (2H, d); 7.26–7.31 (3H, m). MS ESI m/z relative intensity: M+H, 381.2 (100).

2-(N-methylbutylamino)-4-(2-methylimidazol-1-yl)-6-methyl-5-nitropyrimidine Compound n (N-methylbutylamine)—68 mg. ¹H NMR (400 MHz, CDCl₃): δ 0.95 (3H, t); 1.32 (2H, m); 2.51 (3H, br s); 2.55 (3H, s); 3.15–3.24 (3H, d); 3.58–3.72 (2H, t); 6.85 (1H, s); 6.95 (1H, s). MS ESI m/z (relative intensity) M+H, 305.4 (100).

2-(N,N-dibenzylamino)-4-(2-methylimidazol-1-yl)-6-methyl-5-nitropyrimidine Compound o (Dibenzylamine)—20 mg. ¹H NMR (400 MHz, CDCl₃): δ 2.53 (3H, br s); 2.55 (3H, br s); 4.81 (2H, s); 4.96 (2H,s); 6.85 (1H, s); 6.95 (1H, s).

MS ESI m/z (relative intensity) M+H, 415.6 (100).

Compound p (4-methylpiperidine)—45 mg. ¹H NMR (400 MHz, CDCl₃): δ 1.12–1.16 (3H, m); 2.46 (3H, s); 2.51 (3H, s); 3.40–3.47 (8H, m); 6.84 (1H, s); 6.99 (1H, s). MS ESI m/z (relative intensity): M+H, 317.1 (100).

Compound q (N-(cyclopropylmethyl)butylamine)—41 mg. ¹H NMR (400 MHz, CDCl₃): δ 0.23–0.64 (4H, m); 0.89–0.93 (3H, m); 1.18 (1H, t); 1.59–1.73 (2H, m); 2.49–2.51 (3H, d); 2.54–2.55 (3H, d); 3.46–3.58 (2H, m).

MS ESI m/z (relative intensity): M+H, 331.2 (100).

Example 8

This example illustrates the synthesis of 2-(N-methylanilino)-4-pyrrolidino-6-methyl-5-nitropyrimidine (r).

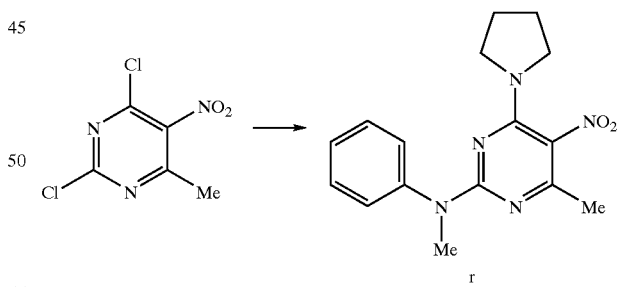

To a cooled (−78° C.) solution of 2,4dichloro-6-methyl-5-nitropyrimidine (208 mg, 1.0 mmol, 1.0 eq. in 2 mL each of EtOH and THF) is added of pyrrolidine (78mg, 1.1 eq) in 1.0 mL of EtOH. The resulting solution is stirred for 1 hour at −78° C., then for 2 hours at 0° C. N-methylaniline (0.432 mL, 4.0 eq.) is added dropwise and the reaction is stirred overnight. The resulting mixture is diluted with dichloromethane, washed with 0.1N HCl, saturated NaCl, dried (MgSO₄), and filtered. Solvent is removed by evaporation and the residue is purified by chromatography to provide the target compound (r).

Example 9

This example illustrates the synthesis of 2-(N-Methyl-N-benzylamino)-4-(2-methylimidazol-1-yl)-5-nitropyrimidine (s).

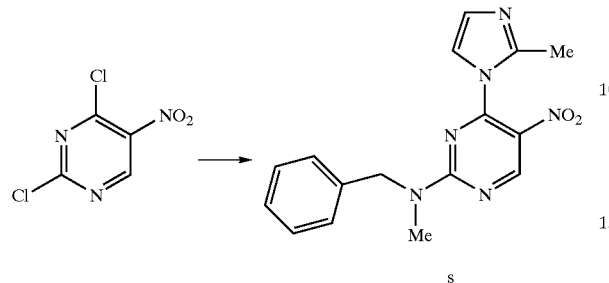

s

To a solution of 2,4dichloro-5-nitropyrimidine (200 mg, 1.0 mmol) in dioxane (5 mL) at 80° C. was added 2-methylimidazole (85 mg, 1.0 mmol) and N-methyl-N-benzylamine (133 µL, 1 mmol). The solution was stirred overnight at 80° C., cooled, and directly chromatographed (1/1 hexane diethyl ether) to yield the title compound (s).

(s) $^1$H NMR (400 MHz) (CD$_3$OD): δ 3.09 (s, 1.5 H), 3.17 (s, 1.5 H), 3.18 (s, 1.5 H), 4.5–4.8 (m, 2H), 7.2–7.5 (m, 8H).

Example 10

This example illustrates the synthesis of 2-(N-Methylanilino)-4-(4-methylimidazol-1-yl)-6-methyl-5-nitropyrimidine (t).

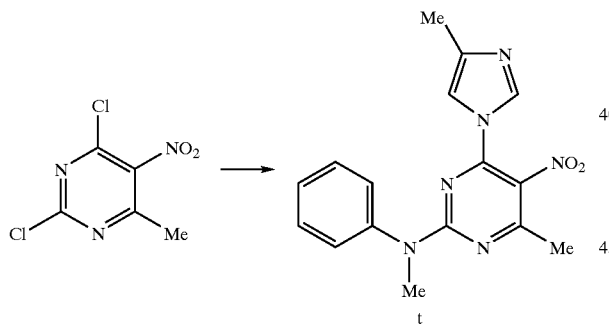

t

To a solution of 2,4dichloro-6-methyl-5-nitropyrimidine (150 mg, 0.72 mmol) in dioxane (5 mL) at 80° C. was added 4-methylimidazole (60 mg, 0.72 mmol) and N-methylaniline (77 mg, 0.72 mmol). The solution was stirred overnight at 80° C., cooled, and directly chromatographed (1/1 hexane diethyl ether) to yield the title compound (t).

(t) $^1$H NMR (400 MHz) (CD$_3$OD): δ 2.37 (s, 3H), 2.74 (s, 3H), 3.30 (s, 3H), 7.25–7.55 (m, 5 H), 7.75 (s, 1 H), 9.31 (s, 1 H).

Example 11

This example illustrates the synthesis of 2-(4-benzylpiperazin-1-yl)-4-(2-methylimidazol-1-yl)-6-methyl-5-nitropyrimidine (u).

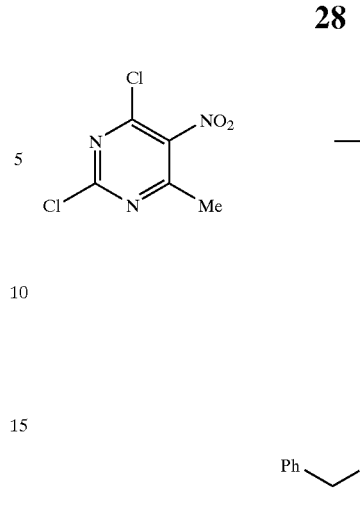

u

To a solution of 2,4dichloro-6-methyl-5-nitropyrimidine (175 mg, 0.84 mmol) in dioxane (5 mL) at 80° C. was added 2-methylimidazole (85 mg, 0.84 mmol) and 1-benzylpiperazine (148 µL, 0.84 mmol). The solution was stirred overnight at 80° C., cooled, and directly chromatographed (1/1 hexane diethyl ether) to yield the title compound (u).

(u) $^1$H NMR (400 MHz) (CD$_3$OD): δ 2.42 (s, 3H), 2.60 (s, 3H), 3.38 (br s, 4H), 3.80 (br s, 4H), 4.38 (s, 2H), 7.30–7.55 (m, 7H). MS ESI 347 m/e (relative intensity): M+H, 348.0 (100).

Example 12

This example illustrates the synthesis of 2-(4-trifluoromethylbenzylamino)-4-(2-methylimidazol-1-yl)-6-methyl-5-nitropyrimidin (v).

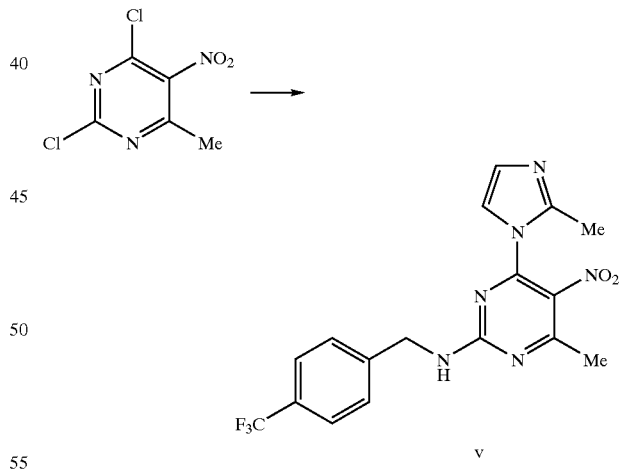

v

To a stirred mixture of 2-chloro-4-hydroxy-6-methyl-5-nitropyrimidine (300 mg, 1.58 mmol, 1.0 eq) in absolute ethanol (20 mL) was added 4-(trifluoromethyl)-benzylamine (540 mg, 3.1 mmol, 2.0 eq), and sodium acetate (130 mg, 1.58 mmol, 1.0 eq). The mixture was slowly heated and the resulting solution refluxed for 22 hours. The mixture was then cooled and ethanol was removed in vacuo. The oily residue was dissolved in ethyl acetate and washed three times with 1M HCl, three times with saturated NaCl solution, then dried over MgSO$_4$. Removal of solvent provided a crude yellow solid intermediate which was dried under vacuum then dissolved in 4 mL of POCl₃ with heating (95–100° C.) for 0.5 hours. The POCl₃ was removed by rotary evaporation and the crude brown product was purified using chromatography (1:1 hexane/dichloromethane) to provide a chloropyrimidine intermediate (313 mg), which was carried on directly without additional purification.

To a stirred solution of the above chloropyrimidine (150 mg, 0.4 mmol, 1.0 eq) in acetonitrile (2.5 mL) was added 2-methylimidazole (142 mg, 1.7 mmol, 4.0 eq). The resulting mixture was heated at reflux for 5 hours, cooled, and the solvent removed by rotary evaporation. The residue was dissolved in ethyl acetate, washed with 0.1M HCl, water, brine and dried over MgSO₄ to give a crude yellow solid following removal of solvent. The solid was purified using chromatography with 2.5% MeOH/dichloromethane to give a yellow oil. The title compound was obtained by precipitation from dichloromethane and hexane. Yield: 152.3 mg, 51% from the starting 2-chloro-4-hydroxy-6-methyl-5-nitropyrimidine.

(v) ¹H NMR (400 MHz) CDCl₃ δ 2.28 (1.5 H, s); 2.42 (1.5 H, s); 2.55 (1.5 H, s); 2.58 (1.5 H, s); 4.71 (1H, d); 4.80 (1H, d); 6.67 (0.5 H, br s); 6.80 (0.5 H,br s); 6.88 (1H, d); 6.96 (1H, s); 7.41 (1H, d); 7.49 (1H, d); 7.62 (2H, d). MS ESI m/z (relative intensity): M+H 392.9 (100).

Example 13

This example illustrates the preparation of 2-((1-phenyl-1-propyl)amino)-4-(imidazol-1-yl)-6-methyl-5-nitropyrimidine (w) using an alternate procedure for the addition of an imidazole group to the pyrimidine nucleus.

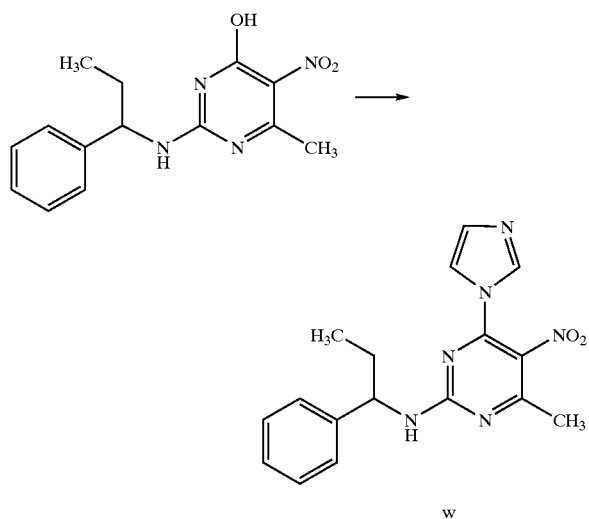

w

To a stirred solution of 2-((1-phenylpropyl)amino)-4-hydroxy-6-methyl-5-nitropyrimidine (78 mg, 0.27 mmol, 1.0 eq, prepared in a manner similar to that in Example 12 above) in pyridine (1 mL) was added trifluoroacetic anhydride (115 μL, 0.81 mmol, 3.0 eq). The mixture was stirred for 15 minutes, then imidazole (184 mg, 2.7 mmol, 10 eq) was added, and the mixture was stirred overnight. Pyridine was removed by rotary evaporation and the dark residue was dissolved in ethyl acetate and washed with 0.1M HCl, followed by brine. The crude solid obtained after removal of solvent was purified by chromatography on silica gel (2.5% MeOH(CH₂Cl₂) to give 36.1 mg (42%) of the title compound.

(w) ¹H NMR (400 MHz) CDCl₃ δ 0.99 (3H, m); 1.73–2.02 (2H, m); 2.48 (3H, s); 4.81 (0.66 H, dd); 5.07 (0.33H, dd); 6.16 (0.66 H, d); 7.02 (0.33H, d); 7.08–7.12 (2H,m); 7.25–7.38 (5 H, m); 7.89 (0.66 H, s); 8.18 (0.33H, s). MS ESI m/z (relative intensity): M+H 339.2 (100).

Example 14

This example illustrates the synthesis of pyrimidine derivatives having an alkoxy group in the 2-position, exemplified by 2-(1-propyloxy)-4-(2-methylimidazol-1-yl)-6-methyl-5-nitropyrimidine (x).

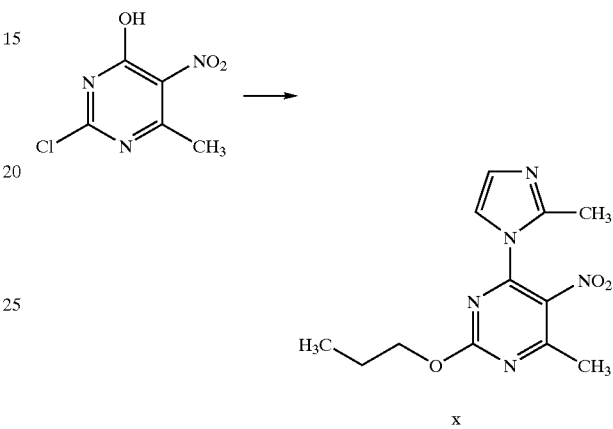

x

To a flask charged with n-propanol (5 mL) was added NaH (128 mg, 60% in oil 3.19 mmol, 2.0 eq) and the mixture was stirred under nitrogen for 10 minutes. The resulting solution was transferred via canula into a flask containing a solution of 2-chloro-4-hydroxy-6-methyl-5-nitropyrimidine (302 mg, 1.6 mmol, 1.0 eq) in n-propanol (5 mL). The resulting mixture was heated in an oil bath at 100° C. for 1 hour, poured into a separatory funnel containing dilute HCl and extracted with dichloromethane. The organic phase was separated and washed with water, brine and dried over MgSO₄ to give a crude solid (yield 297 mg) after removal of solvent. The crude solid was heated in neat POCl₃ (3 mL) for 6 minutes at 85–90° C., cooled on ice, and the POCl₃ was removed in vacuo. The chloropyrimidine intermediate was purified via chromatography to provide 117 mg of the intermediate which was converted to the title compound using methods described in Example 12. The product was obtained as a yellow oil (191 mg, 43% from 2-chloro-4-hydroxy-6-methyl-5-nitropyrimidine).

(x) ¹H NMR (400 MHz) CDCl₃ δ 1.04 (3H, t); 1.86 (2H, dq); 2.52 (3H, s); 2.61 (3H, s); 4.38 (2H, t); 6.90 (1H, d); 6.98 (1H, d). MS ESI m/z (relative intensity): M+H 278.1 (100).

Example 15

The compounds listed in Table 2 were prepared using the procedures outlined in Examples 12–13. Compounds were tested in the CMV assay described above and exhibited the following levels of activity: +, IC₅₀>500 nM; ++, 100 nM<IC₅₀≦500 nM; +++, IC₅₀≦100 nM.

TABLE 2
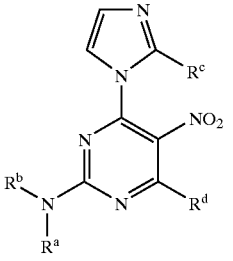
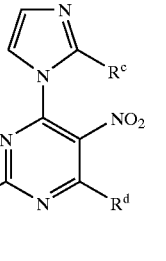

TABLE 2-continued
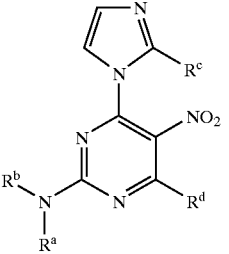
| $R^a$ | $R^b$ | $R^c$ | $R^d$ | m/z (m + 1) | Antiviral Activity |
|---|---|---|---|---|---|
| 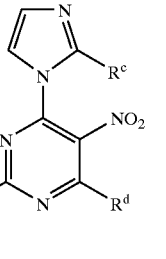 | H | Me | Me | 343.1 | ++ |
| 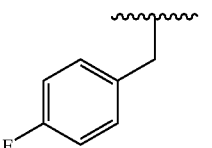 | H | Me | Me | 393.1 | ++ |
| 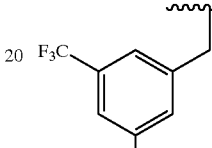 | H | Me | Me | 359.1 | +++ |
| 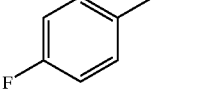 | H | Me | Me | 359.1 | ++ |
| 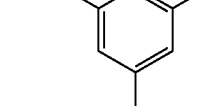 | H | Me | Me | 392.1 | +++ |
| 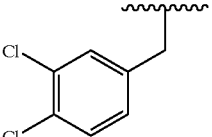 | H | Me | Me | 339.1 | + |
| 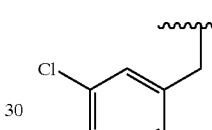 | H | Me | Me | 359.1 | +++ |
| 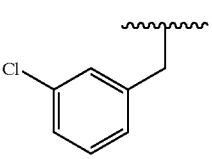 | H | Me | Me | 461.1 | + |
| 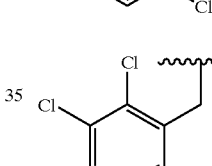 | H | Me | Me | 393.1 | +++ |
| 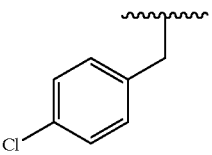 | H | Me | Me | 393.1 | ++ |
| 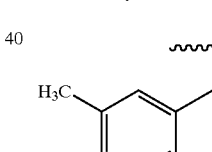 | H | Me | Me | 339.1 | ++ |
| 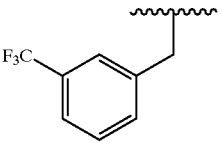 | H | Me | Me | 403.0 | +++ |
| 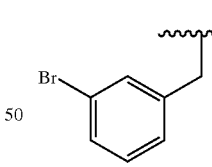 | H | Me | Me | 343.1 | ++ |
| 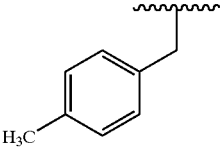 | H | Me | Me | 355.1 | ++ |

TABLE 2-continued

Structure: pyrimidine with imidazole (bearing R^c) at position 4, NO_2 at position 5, R^d at position 6, and N(R^a)(R^b) at position 2.

| R^a | R^b | R^c | R^d | m/z (m + 1) | Antiviral Activity |
|---|---|---|---|---|---|
| pyridin-3-ylmethyl | H | Me | Me | 326.1 | + |
| pyridin-2-ylmethyl | H | Me | Me | 326.1 | ++ |
| 3,4-dimethoxybenzyl | H | Me | Me | 385.1 | ++ |
| 3,4,5-trifluorobenzyl | H | Me | Me | 379.1 | ++ |
| 2,3,6-trifluorobenzyl | H | Me | Me | 379.1 | ++ |
| 2,3,5-trifluorobenzyl | H | Me | Me | 379.1 | ++ |
| 2,3,4-trifluorobenzyl | H | Me | Me | 379.1 | ++ |
| 3,4-difluorobenzyl | H | Me | Me | 361.1 | ++ |
| 2-fluoro-5-(trifluoromethyl)benzyl | H | Me | Me | 411.1 | +++ |
| 2-chloro-6-methylbenzyl | H | Me | Me | 373.1 | ++ |
| 2-methylbenzyl | H | H | Me | 325.1 | + |
| 2-methylbenzyl | H | Me | Me | 339.1 | ++ |
| 2,5-difluorobenzyl | H | Me | Me | 361.1 | ++ |

Example 16

The compounds listed in Table 3 were prepared using procedures similar to those outlined in Examples 12–14. Compounds were tested in the CMV assay described above and exhibited the following levels of activity: +, $IC_{50} > 500$ nM.

TABLE 3

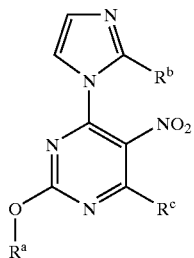

| R$^a$ | R$^b$ | R$^c$ | m/z (m + 1) | Antiviral Activity |
|---|---|---|---|---|
| n-propyl | Me | Me | 278.1 | + |
| n-propyl | H | Me | 264.1 | + |
| n-butyl | Me | Me | 292.2 | + |
| n-butyl | H | Me | 278.1 | + |
| phenethyl | H | Me | 326.1 | + |
| methyl | Me | Me | 250.1 | + |
| ethyl | Me | Me | 264.1 | + |
| benzyl | H | Me | 312.2 | + |
| 3-methoxy-1-butyl | H | Me | 308.1 | + |
| 3-methoxy-1-butyl | Me | Me | 322.3 | + |
| 3,3-dimethyl-1-butyl | H | Me | 306.2 | + |
| 3,3-dimethyl-1-butyl | Me | Me | 320.1 | + |

Example 17

This example illustrates the synthesis of 2-(2-indanamino)-4-(2-methylimidazol-1-yl)-6-methyl-5-nitropyrimidine.

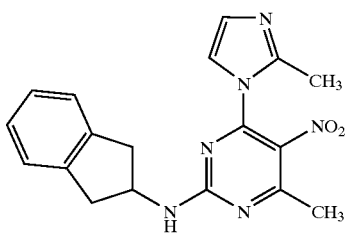

2-(2-Indanamino)-4-chloro-6-(methyl-5-nitropyrimidine prepared according to the procedure of Example 12, but using 2-indanamine as the nucleophile, (56 mg, 0.18 mmol) was dissolved in 2.0 mL EtOH followed by the addition of 2-methylimidazole (38 mg, 0.46 mmol, 2.5 equiv). The resulting yellow solution was placed in an 80° C. bath and allowed to stir for 24 hours. The solution was then concentrated under reduced pressure. Purification by flash chromatography (SiO$_2$, 2% MeOH/CH$_2$Cl$_2$) gave 34 mg of the (52%) title compound as an amorphous yellow: mp 203–204° C.

$^1$H NMR (CDCl$_3$, 400 MHz, mixture of rotamers) δ 7.28–7.13 (m, 5 H), 6.99 (s, 0.5 H), 6.96 (s, 0.5 H), 6.17 (d, J=7.9 Hz, 0.5 H), 6.06 (d, J=7.3 Hz, 0.5 H), 4.93 (m, 0.5 H), 4.73 (m, 0.5 H), 3.45–3.34 (m, 2H), 2.94 (dd, J=4.8, 16.2 Hz, 1 H), 2.89 (dd, J=4.3, 16.0 Hz, 1 H), 2.71 (s, 1.5 H), 2.65 (s, 1.5 H), 2.63, s, 1.5 H), 2.53 (s, 1.5 H); MS ESI m/z (relative intensity): 351.2 (M+H, 100). Anal. calcd for C$_{18}$H$_{18}$N$_6$O$_2$: C, 61.70; H, 5.18; N, 23.99. Found: C, 61.08; H, 5.22; N, 23.57.

Example 18

This example illustrates the synthesis of 2-(2-indanamino)-4-imidazol-1-yl-6-methyl-5-nitropyriridine.

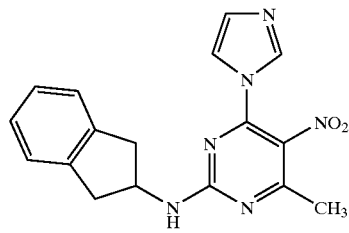

2-(2-Indanamino)-4-chloro-6-methyl-5-nitropyrimidine (66.8 mg, 0.22 mmol) was dissolved in 2.0 mL EtOH followed by the addition of imidazole (37 mg, 0.54 mmol, 2.5 equiv). The yellow solution was heated to 80° C. for 18 hours. The solution was then concentrated under reduced pressure and purified by flash chromatography (SiO$_2$, 2% MeOH/CH$_2$Cl$_2$) to give 52.1 mg (71%) of the product as an amorphous yellow solid (0.155 mmol): mp 177–178° C.

$^1$H NMR (CDCl$_3$, 400 MHz, mixture of rotamers) δ 8.23 (s, 0.5 H), 8.16 (s, 0.5 H), 7.28–7.11 (m, 6 H), 6.09 (broad s, 0.5 H), 5.91 (d, J=7.2 Hz, 0.5 H), 4.93 (m, 0.5 H), 4.79 (m, 0.5 H), 3.40 (dd, J=7.0, 15.9 Hz, 2H), 2.91 (dd, J=4.1, 15.8 Hz, 2H), 2.56 (s, 1.5 H), 2.46 (s, 1.5 H); ); MS ESI(relative abundance) 337.1 (M+H, 100). Anal. calcd for C$_{17}$H$_{16}$N$_6$O$_2$: C, 60.71; H, 4.79; N, 24.99. Found: C, 60.29; H, 4.89; N, 24.69.

Example 19

This example illustrates the synthesis of 2-(4,6-difluoro-1-indanamino)-4-(imidazol-1-yl)-6-methyl-5-nitropyrimidine.

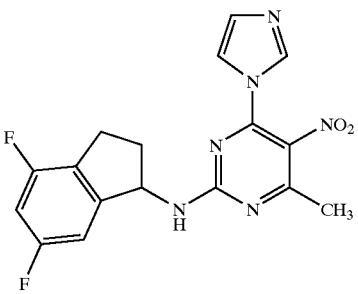

2-(4,6-Difluoro-1-indanamino)-4-chloro-6-methyl-5-nitropyrimidine prepared according to the procedure of Example 12, using 4,6-difluoro-1-indanamine as the nucleophile (56 mg, 0.16 mmol) was dissolved in 2.0 mL EtOH followed by the addition of imidazole (28 mg, 0.411 mmol, 2.5 equiv). The solution was heated to 80° C. for 23 hours. The solution was then concentrated under reduced pressure and purified by flash chromatography (SiO$_2$, 2% MeOH/CH$_2$Cl$_2$) to give 35.5 mg (58% yield) of the product as an amorphous yellow solid. mp 175–176° C.

$^1$H NMR (CDCl$_3$, 400 MHz, mixture of rotamers) δ 8.09 (s, 0.5 H), 8.06 (s, 0.5 H), 7.26–7.10 (m, 2H), 6.82 (dd, J=7.6, 11.6 Hz, 1 H), 6.72 (dd, J=8.8, 8.8 Hz, 1 H), 5.95 (broad s, 0.5 H), 5.82 (d, J=8.4 Hz, 0.5 H), 5.72 (m, 0.5 H), 5.56 (m, 0.5 H), 3.05 (m, 1 H), 2.87 (m, 1 H), 2.73 (m, 1 H), 2.55 (s, 1.5 H), 2.49 (s, 1.5 H), 1.98 (m, 1 H); ); MS ESI(relative abundance) 373.1 (M+H, 100). Anal. calcd for $C_{17}H_{14}F_2N_6O_2$: C, 54.84; H, 3.79; N, 22.57. Found: C, 54.95; H, 3.76; N, 22.32.

Example 20

This example illustrates the synthesis of 2-(4,6-difluoro-1-indanamino)-4-(2-methylimidazol-1-yl)-6-methyl-5-nitropyrimidine

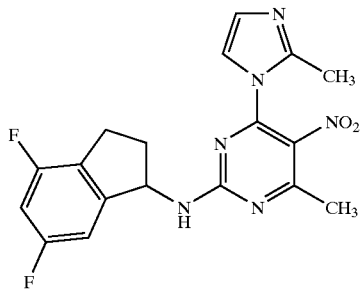

2-(4,6-Difluoro-1-indanamino)-4chloro-6-methyl-5-nitropyrimidine (56 mg, 0.16 mmol) was dissolved in 2.0 mL EtOH followed by the addition of 2-methylimidazole (34 mg, 0.41 mmol, 2.5 equiv) and the solution was heated to 80° C. with stirring for 26 hours. The solution was then concentrated under reduced pressure and purified by flash chromatography ($SiO_2$, 2% $MeOH/CH_2Cl_2$) to give 42.6 mg (67% yield) of the as an amorphous yellow solid. mp 164–165° C.

$^1$H NMR ($CDCl_3$, 400 MHz, mixture of rotamers) δ 6.98 (s, 1 H), 6.90 (s, 1 H), 6.81 (m, 1 H), 6.71 (m, 1 H), 5.87–5.81 (m, 1 H), 5.73 (m, 0.5 H), 5.54 (m, 0.5 H), 3.05 (m, 1 H), 2.82 (m, 1 H), 2.70 (m, 1 H), 2.60 (s, 1.5 H), 2.53 (s, 1.5 H), 2.51 (s, 1.5 H), 2.46 (s, 1.5 H), 1.98 (m, 1 H); ); MS ESI(relative abundance) 387.1 (M+H, 100). Anal. calcd for $C_{18}H_{16}F_2N_6O_2$: C, 55.96; H, 4.17; N, 21.75. Found: C, 56.15; H, 4.59; N, 20.71.

Example 21

This example illustrates the synthesis of 2-(4,6-difluoro-1-indanamino)-4-(2-ethylimidazol-1-yl)-6-methyl-5-nitropyrimidine.

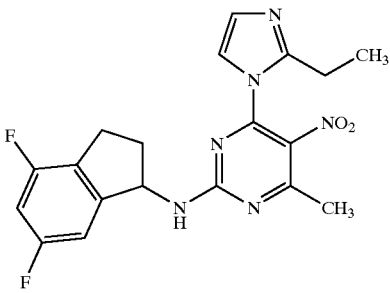

2-(4,6-Difluoro-1-indanamino)-4-chloro-6-methyl-5-nitropyrimidine (56 mg, 0.16 mmol) was dissolved in 2.0 mL EtOH followed by the addition of 2-ethylimidazole (39 mg, 0.41 mmol, 2.5 equiv) and the solution was heated to 80° C. for 23.5 hours. The solution was then concentrated under reduced pressure and purified by flash chromatography ($SiO_2$, 2% $MeOH/CH_2Cl_2$) to give 39.6 mg (60% yield) of the product as an amorphous yellow solid: mp 88–89° C.

$^1$H NMR ($CDCl_3$, 400 MHz, mixture of rotamers) δ 7.02 (s, 1 H), 6.88 (s, 1 H), 6.81 (m, 1 H), 6.72 (m, 1 H), 5.85 (d, J=9.0 Hz, 0.5 H), 5.81–5.70 (m, 1 H), 5.55 (m, 0.5 H), 3.04 (m, 1 H), 2.86–2.64 (m, 4H), 2.60 (s, 1.5 H), 2.53 (s, 1.5 H), 1.98 (m, 1 H), 1.29 (t, J=7.5 Hz, 3H); MS ESI(relative abundance): 401.1 (M+H, 100). Anal. calcd for $C_{19}H_{18}F_2N_6O_2$: C, 57.00; H, 4.53; N, 20.99. Found: C, 56.93; H, 4.50; N, 20.71.

Example 22

This example illustrates the synthesis of 2-(2-indanamino)-4-(2-methylimidazol-1-yl)-6-methyl-5-nitropyrimidine, monohydrochloride salt.

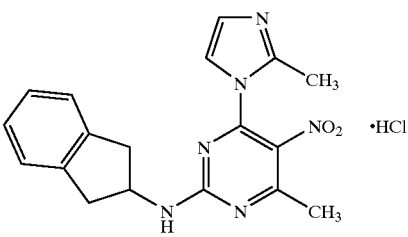

2-(2-Indanamino)-4-chloro-6-methyl-5-nitropyrimidine (310 mg, 1.02 mmol) prepared in Example 17 was dissolved in 7 mL EtOH followed by the addition of 2-methylimidazole (600 mg, 7.3 mmol, 7.2 equiv). The resulting yellow solution was then heated at 80° C. with magnetic stirring. After 24 hours the solution was concentrated under reduced pressure and purified by flash chromatography ($SiO_2$, 2% $MeOH/CH_2Cl_2$) to give 303.6 mg of the free base as a yellow solid (0.867 mmol). The yellow solid was then dissolved in 3 mL anhydrous THF followed by the addition of 2 mL (8.0 mmol, 9.2 equiv) of a 4.0 M solution of HCl in 1,4-dioxane. A precipitate was immediatly formed, and the resulting slurry was allowed to stir for 10 min. The slurry was then concentrated under reduced pressure, taken up in 3 mL THF, and concentrated again. The resulting yellow solid was recrystallized from hot EtOAc to give 179 mg (45% yield) of the hydrochloride salt as light yellow needles: mp 184–185° C.

$^1$H NMR ($CD_3OD$, 400 MHz, mixture of rotamers) δ 7.76 (d, J=2.2 Hz, 0.5 H), 7.71 (d, J=2.2 Hz, 0.5 H), 7.64 (d, J=2.2 Hz, 0.5 H), 7.61 (d, J=2.2 Hz, 0.5 H), 7.22 (m, 2H), 7.15 (m, 2H), 4.92 (m, 0.5 H), 4.72 (m, 0.5 H), 3.41–3.31 (m, 1 H), 2.97 (m, 1 H), 2.73 (s, 1.5 H), 2.72 (s, 1.5 H), 2.68 (s, 1.5 H), 2.65 (s, 1.5 H). Anal. calcd for $C_{18}H_{18}N_6O_2 \cdot HCl$: C, 55.89; H, 4.95; N, 21.73; Cl, 9.16. Found: C, 55.89; H, 5.00; N, 21.56; Cl, 9.14.

Example 23

This example illustrates the synthesis of 2-(cis-2-ethylcyclohexylamino)-4-imidazol-1-yl-6-methyl-5-nitropyrimidine.

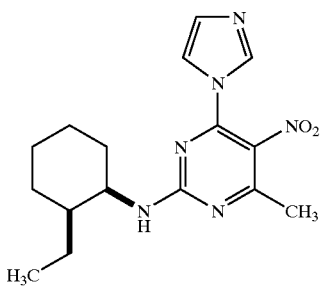

2-(cis-2-Ethylcyclohexylamino)-4-chloro-6-methyl-5-nitropyrimidine (58.6 mg, 0.196 mmol) was dissolved in 2.0 mL EtOH followed by the addition of imidazole (53 mg, 0.78 mmol, 4.0 equiv). The resulting yellow solution was then heated to 80° C. with magnetic stirring. After 20 hours the solution was concentrated under reduced pressure and purified by flash chromatography ($SiO_2$, 2% MeOH/$CH_2Cl_2$) to give 39.5 mg (61% yield) of the title compound as an amorphous yellow solid: mp 123–124° C.

$^1$H NMR ($CDCl_3$, 400 MHz, mixture of rotamers) δ 8.22 (s, 0.5 H), 8.17 (s, 0.5 H), 7.39–7.27 (m, 2H), 5.92 (d, J=7.8 Hz, 1 H), 4.57 (m, 0.5 H), 4.42 (m, 0.5 H), 2.65 (s, 1.5 H), 2.61 (m, 1.5 H), 2.02 (m, 1 H), 1.87–1.34 (m, 10H), 1.02 (t, J=7.0 Hz, 3H); MS ESI(relative abundance): 331.2 (M+H, 100). Anal. calcd for $C_{16}H_{22}N_6O_2$: C, 58.17; H, 6.71; N, 25.44. Found: C, 58.01; H, 6.79; N, 25.30.

Example 24

The compounds listed in Table 4 were prepared using the procedures outlined in Examples 17–23. Compounds were tested in the CMV assay described above and exhibited the following levels of activity: +, $IC_{50}$>500 nM; ++, 100 nM<$IC_{50}$≦500 nM; +++, $IC_{50}$≦100 nM.

TABLE 4

| $R^a$ | $R^b$ | $R^c$ | $R^d$ | m/z (m + 1) or mp (° C.) | Antiviral Activity |
|---|---|---|---|---|---|
| indanyl | H | Me | Me | 351.2 | +++ |
| indanyl (other stereo) | H | Me | Me | 351.2 | +++ |
| indanyl | H | Me | Me | 351.2 | +++ |
| tetrahydronaphthyl | H | Me | Me | 365.1 | ++ |
| indanyl | Me | Me | Me | 365.1 | ++ |
| chloro-indanyl | H | Me | Me | 385.1 | + |
| indanyl | | Me | Me | 181–182° C. | ++ |
| indan-2-yl | H | Me | Me | 203–204° C. | + |
| indan-2-yl | H | H | Me | 177–178° C. | + |

TABLE 4-continued

[Structure: 4-(2-R^c-imidazol-1-yl)-5-nitro-6-R^d-2-(N(R^a)(R^b))-pyrimidine]

| R^a | R^b | R^c | R^d | m/z (m + 1) or mp (° C.) | Antiviral Activity |
|---|---|---|---|---|---|
| 2,3-dihydrobenzofuran-3-yl | H | Me | Me | 353.1 | ++ |
| 4,6-difluoroindan-1-yl | H | Et | Me | 88–89° C. | ++ |
| 4,6-difluoroindan-1-yl | H | H | Me | 175–176° C. | ++ |
| 4,6-difluoroindan-1-yl | H | Me | Me | 164–165° C. | ++ |
| 5,6-difluoroindan-1-yl | H | H | Me | 189–190° C. | ++ |
| 5,6-difluoroindan-1-yl | H | Et | Me | 177–178° C. | ++ |
| 5,6-difluoroindan-1-yl | H | Me | Me | 205–206° C. | ++ |
| indan-2-yl | H | Et | Me | 187–188° C. | + |
| 4,7-difluoroindan-1-yl | H | H | Me | 153–154° C. | ++ |
| 4,7-difluoroindan-1-yl | H | Me | Me | 140–141° C. | +++ |
| 4,7-difluoroindan-1-yl | H | Et | Me | 158–159° C. | +++ |
| 4-fluoroindan-1-yl | H | H | Me | 178–179° C. | ++ |
| 4-fluoroindan-1-yl | H | Me | Me | 74–75° C. | ++ |

TABLE 4-continued

| $R^a$ | $R^b$ | $R^c$ | $R^d$ | m/z (m + 1) or mp (° C.) | Antiviral Activity |
|---|---|---|---|---|---|
| 4-F-indanyl | H | Et | Me | 65–66° C. | ++ |
| 6-Br-indanyl | H | Me | Me | 429.1 | ++ |
| indanyl | H | H | Me | 337.1 | +++ |
| 6-Cl-indanyl | H | Me | Me | 385.1 | ++ |
| 6-F-indanyl | H | H | Me | 355.1 | +++ |
| 6-F-indanyl | H | Me | Me | 369.2 | ++ |
| 1-methoxy-indanyl (2-yl) | H | H | Me | 367.3 | + |
| 1-methoxy-indanyl (2-yl) | H | Me | Me | 381.2 | + |
| indanyl | H | Et | Me | 365.1 | ++ |
| trans-2-hydroxy-indanyl | H | Me | Me | 367.3 | +++ |
| indanyl | H | Me | H | 337.1 | ++ |
| 2-hydroxy-indanyl | H | H | Me | 353.1 | ++ |
| 1,1-dimethyl-indan-2-yl | H | H | Me | 365.1 | + |

TABLE 4-continued

[Structure: pyrimidine with imidazole substituted with R^c, NO2, R^d, and NR^aR^b groups]

| R^a | R^b | R^c | R^d | m/z (m + 1) or mp (° C.) | Antiviral Activity |
|---|---|---|---|---|---|
| [1,1-dimethylindan-2-yl] | H | Me | Me | 379.2 | ++ |
| [2-hydroxyindan-1-yl] | H | Me | Me | 367.2 | |
| [6-fluorochroman-4-yl] | H | H | Me | 371.1 | |
| [6-fluorochroman-4-yl] | H | Me | Me | 385.2 | |

Example 24

The compounds provided in this example were prepared using procedures outlined above. The starting materials are available as described above, or from commercial sources.

24.1 2-(N-(trans-2-methylcyclohexyl)amino)-4-(2-methylimidazol-1-yl)-6-methyl-5-nitropyrimidine $^1$H NMR (400 MHz, CDCl$_3$): δ 0.92 (1.5 H, d, J=7.2 Hz); 0.94 (1.5 H, d, J=7.2 Hz); 1.00–1.30 (5 H, m); 1.31–1.41 (1H, m); 1.74–1.82 (2H, m); 1.94–1.96 (1H, m); 2.39 (1.5 H, s); 2.47(1.5 H, s); 2.48(1.5 H, s); 2.53 (1.5 H, s); 3.52 (0.5 H, dq, J=4.0, 9.8 Hz); 3.69 (0.5 H, dq, J=4.0, 9.8 Hz); 5.86 (0.5 H, d, J=9.2 Hz), 5.98 (0.5 H, d, J=9.2 Hz); 6.86 (1H, s); 6.93 (0.5 H, s); 6.95 (0.5 H, s). MS ESI: m/z (relative intensity): M+H, 331.2 (100).

24.2 2-(N-(cis-2-methylcyclohexyl)amino)-4-(2-methylimidazol-1-yl)-6-methyl-5-nitropyrimidine $^1$H NMR (400 MHz, CDCl$_3$): δ 0.93 (3H, d, J=7.2 Hz); 1.22–1.41 (3H, m); 1.48–1.68 (4H, m); 1.71–1.78 (1H, m); 1.95 (1H, m); 2.44 (1.5 H, s); 2.51 (3H, s); 2.57 (1.5 H, s); 4.13 (0.5 H, m); 4.28 (0.5 H, m); 5.68 (0.5 H, d, J=9.0 Hz), 5.59 (0.5 H, d, J=9.0 Hz); 6.87 (1H, s); 6.94 (0.5 H, s); 6.96 (0.5 H, s). MS ESI: m/z (relative intensity): M+H, 331.2 (100)

24.3 2-(N-(trans-2-methylcyclohexyl)amino)-4-(imidazol-1-yl)-6-methyl-5-nitropyrimidine $^1$H NMR (400 MHz, CDCl$_3$): δ 0.96 (3H, d, J=6.5 Hz); 1.11–1.29 (3H, m); 1.33–1.39 (2H, m); 1.70 (1H, m); 1.75–1.83 (2H, m) 2.05 (1H, dd, J=2.8, 13.4 Hz); 2.45 (1.5 H, s); 2.50 (1.5 H, s); 3.54 (0.5 H, dq, J=4.0, 9.8 Hz); 3.70

(0.5 H, dq, J=4.0, 9.8 Hz); 5.43 (0.5 H, s), 5.46 (0.5 H, s); 7.12 (0.5 H, s); 7.15 (0.5 H, s); 7.17 (0.5 H, s); 7.18 (0.5 H, s); 8.04 (0.5 H, s); 8.08 (0.5 H, s). MS ESI: m/z (relative intensity): M+H, 317.2 (100).

24.4 2-(cis-2-methylcyclohexyl)amino)-4-(imidazol-1-yl)-6-methyl-5-nitropyrimidine

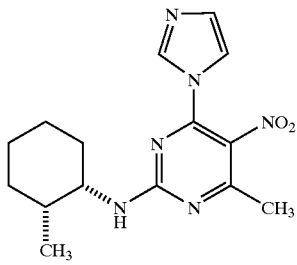

¹H NMR (400 MHz, CDCl₃): δ 0.93 (3H, d, J=7.2 Hz); 1.22–1.41 (3H, m); 1.48–1.68 (4H, m); 1.76–1.82 (1H, m); 1.94–1.99 (1H, m); 2.48 (1.5 H, s); 2.52 (1.5 H, s); 4.15 (0.5 H, m); 4.29 (0.5 H, m); 5.65 (0.5 H, d, J=7.6 Hz), 5.73 (0.5 H, d, J=7.6 Hz); 7.16 (1H, s); 7.21 (1H, s); 8.04 (0.5 H, s); 8.10 (0.5 H, s). MS SEI m/z relative intensity:M+H, 317.2 (100)

24.5 2-(N-(trans-2-methyl-4-cyclohexenyl)amino)-4-(imidazol-1-yl)-6-methyl-5-nitropyrimidine

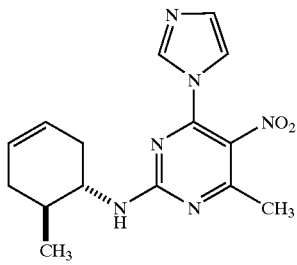

¹H NMR (400 MHz, CDCl₃): δ 0.93 (1.5 H, d, J=6.8 Hz); 1.00 (1.5 H, d, J=6.8 Hz); 1.22 (1H, m); 1.83–1.88(1H, m); 1.93–2.00 (1H, m); 2.12 (1H, m) 2.27 (1H, m); 2.44 (1.5 H, s); 2.49 (1.5 H, s); 3.93 (0.5 H, dq, J=1.2, 7.2 Hz); 4.08 (0.5 H, dq J=1.2, 7.2 Hz); 5.51 (0.5 H, d, J=7.0 Hz); 5.60 (1.5 H, m); 5.68 (0.5 H, m); 7.13 (1H, s); 7.16 (1H, s); 8.00 (0.5 H, s); 8.07 (0.5 H, s). MS ESI: m/z (relative intensity): M+H, 315.2 (100).

24.6 2-(N-(cis-2-methylcyclohexenyl)amino)-4-(imidazol-1-yl)-6-methyl-5-nitropyrimidine

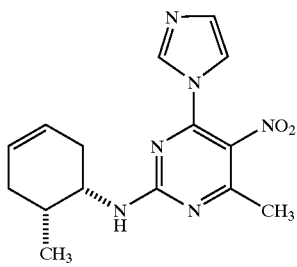

¹H NMR (400 MHz, CDCl₃): δ 0.96 (3H, d, J=6.8 Hz); 1.26 (1H, m); 1.84–1.92 (1H, m); 2.10–2.18 (1H, m); 2.27 (1H, m) 2.42 (1H, m); 2.47 (1.5 H, s); 2.51 (1.5 H, s); 4.32 (0.5 H, m); 4.47 (0.5 H, m); 5.63 (1H, s), 5.72 (1H, s); 5.79 (0.5 H, d, J=9.0 Hz); 5.88 (0.5 H, d, J=9.0 Hz); 7.13 (0.5 H, s); 7.15 (0.5 H, s); 7.17 (0.5 H,s); 7.21 (0.5 H, s); 8.03 (0.5 H, s); 8.08 (0.5 H, s). M ESI: m/z (relative intensity): M+H, 315.2 (100).

24.7 2-(N-(trans-3-methylcyclohexyl)amino)-4-(imidazol-1-yl)-6-methyl-5-nitropyrimidine

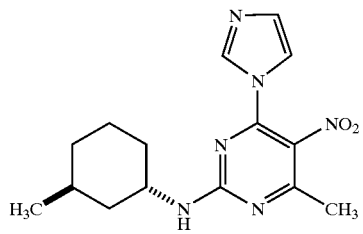

¹H NMR (400 MHz, CDCl₃): δ 0.93 (1.5 H, d, J=6.5 Hz); 0.96 (0.5 H, d, J=6.5 Hz); 1.01–1.12 (1H, m); 1.33–1.41 (1H, m); 1.45–1.54 (1H, m); 1.60–1.83 (5 H, m); 2.40 (1.5 H, s); 2.49 (1.5 H, s); 2.50 (1.5 H, s); 2.56 (1.5 H, s); 4.19 (0.5 H, m); 4.32 (0.5 H, m); 5.98 (0.5 H, d, J=6.0 Hz), 6.03 (0.5 H, d, J=6.0 Hz); 6.88 (1H, s); 6.96 (1H, s). MS ESI: m/z (relative intensity): M+H, 331.2 (100).

24.8 2-(N-cis-3-methylcyclohexyl)amino)-4-(imidazol-1-yl)-6-methyl-5-nitropyrimidine

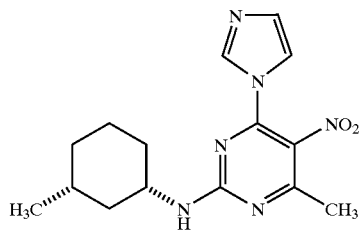

¹H NMR (400 MHz, CDCl₃): δ 0.90 (3H, d, J=6.5 Hz); 1.08 (1H, m); 1.29–1.38 (1H, m); 1.42–1.52 (1H, m); 1.60–1.70 (1H, m); 1.76 (1H, m); 1.92–2.03 (4H, m); 2.36 (1.5 H, s); 2.46 (1.5 H, s); 2.49 (1.5 H, s); 2.54 (1.5 H, s); 3.73 (0.5 H, m); 3.91 (0.5 H, m); 6.06 (0.5 H, bs), 6.22 (0.5 H, bs); 6.85 (1H, s); 6.93 (1H, s).

MS ESI: m/z (relative intensity): M+H, 331.2 (100).

24.9 2–Cyclohexylamino-4-(2-methylimidazol-1-yl)-6-methyl-5-nitropyrimidine

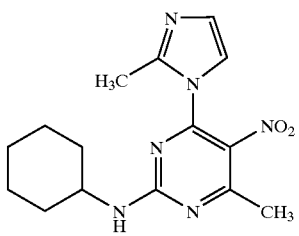

¹H NMR (400 MHz, CDCl₃): δ 1.39 (2H, m); 1.53 (2H, m); 1.74 (2H, m); 1.90 (2H, m); 2.15 (2H, m); 2.58 (1.5 H, s); 2.65 (1.5 H, s); 2.67 (1.5 H, s); 2.72 (1.5 H, s); 3.95 (0.5

H, m); 4.10 (0.5 H, m); 5.68 (0.5 H, d, J=4.0 Hz), 5.79 (0.5 H, d, J=4.0 Hz); 7.03 (1H, s); 7.12 (1H, s).

MS ESI: m/z (relative intensity): M+H, 317.2 (100).

24.10 2–Cyclohexylmethylamino-4-(imidazol-1-yl)-6-methyl-5-nitropyrimidine

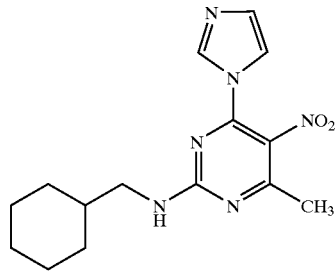

$^1$H NMR (400 MHz, CDCl$_3$): δ 0.93–1.03 (2H, m); 1.12–1.28 (3H, m); 1.50–1.61 (1H, m); 1.53–1.80 (5 H, m); 2.44 (1.5 H, s); 2.50 (1.5 H, s); 3.31 (2H, dt, J=6.5, 24 Hz); 5.88 (0.5 H, bs); 6.40 (0.5 H, bs); 7.10 (0.5 H, s); 7.13 (1.5 H, s), 7.19 (0.5 H, s); 8.07 (1H, s).

MS ESI m/z (relative intensity):M+H, 317.2 (100)

24.11 2–Cyclohexylmethylamino-4-(2-methylimidazol-1-yl)-6-methyl-5-nitropyrimidine

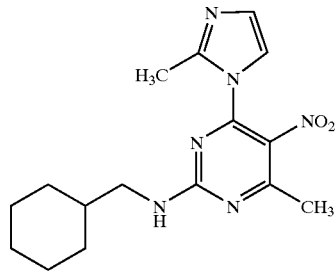

$^1$H NMR (400 MHz, CDCl$_3$): δ 0.96 (2H, m); 1.14–1.30 (4H, m); 1.55 (1H, m); 1.67 (1H, m); 1.67–1.80 (5 H, m); 2.39 (1.5 H, s); 2.47 (1.5 H, s); 2.49 (1.5 H, s); 2.54 (1.5 H, s); 3.25 (0.5 H, t, J=6.3 Hz); 3.35 (0.5 H, t, J=6.3 Hz); 6.02 (1H, bs), 6.86 (1H, s); 6.95 (1H, s).

MS ESI m/z (relative intensity): M+H, 331.2 (100).

24.12 2-Cyclopentylamino-4-(2-methylimidazol-1-yl)-6-methyl-5-nitropyrimidine

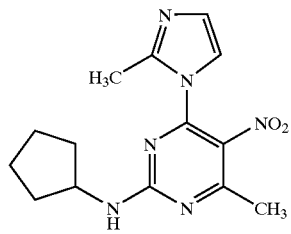

$^1$H NMR (400 MHz, CDCl$_3$): δ 1.21 (1H, m); 1.49 (1H, m); 1.60–1.78 (4H, m); 2.38 (1.5 H, s); 2.47 (1.5 H, s); 2.55 (1.5 H, s); 4.21 (0.5 H, m); 4.37 (0.5 H, m); 5.86 (0.5 H, d, J=4.2 Hz); 5.98 (0.5 H, d, J=4.2 Hz); 6.86 (1H, s); 6.95 (1H, s). MS ESI: m/z (relative intensity): M+H, 303.2 (100).

24.13 2-(N-(4-Methylcyclohexyl)amino)-4-(imidazol-1-yl)-6-methyl-5-nitropyrimidine

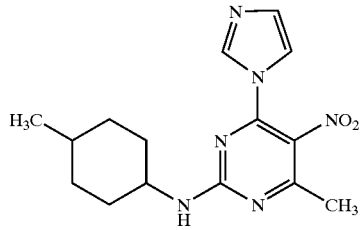

$^1$H NMR (400 MHz, CDCl$_3$): δ 1.03 (1.5 H, d, J=6.2 Hz); 1.06 (1.5 H, d, J=6.2 Hz); 1.08 (1H, m); 1.15–1.28 (1H, m); 1.30–1.42 (2H, m); 1.43–1.55 (1H, m); 1.70–1.84 (4H, m); 1.85–1.96 (2H, m); 2.18 (1H, m); 2.54 (1.5 H, s); 2.64 (3H, s); 2.69 (1.5 H, s); 3.84 (0.5 H, m); 4.02 (0.5 H, m); 5.97 (0.5 H, bs), 6.11 (0.5 H, bs); 7.01 (1H, s); 7.10 (1H, s).

MS ESI: m/z (relative intensity): M+H, 331.1 (100).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

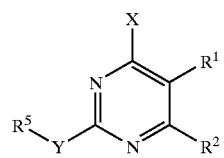

(I)

wherein

X is a member selected from the group consisting of —NR$^3$R$^4$, —OR$^3$, —SR$^3$, aryl, alkyl and arylalkyl;

Y is a member selected from the group consisting of a covalent bond, —NR$^6$)—, —O—, —S—, —C(=O)— and alkylene;

R$^1$ and R$^2$ are members independently selected from the group consisting of hydrogen, alkyl, —O-alkyl, —S-alkyl, aryl, arylalkyl, —O-aryl, —S-aryl, —NO$_2$, —NR$^7$R$^8$, —C(O)R$^9$, —CO$_2$R$^{10}$, —C(O)NR$^7$R$^8$, —N(R$^7$)C(O)R$^9$, —N(R$^7$)CO$_2$R$^{11}$, —N(R$^9$)C(O) NR$^7$R$^8$, —S(O)$_m$NR$^7$R$^8$, —S(O)$_n$R$^9$, —CN, halogen, and —N(R$^7$)S(O)$_m$R$^{11}$;

R$^3$ and R$^4$ are members independently selected from the group consisting of hydrogen, alkyl, aryl and arylalkyl, or taken together with the nitrogen atom to which each is attached form a 5-, 6- or 7-membered aromatic or non-aromatic ring containing from one to three heteroatoms selected from the group consisting of N, O and S;

R$^5$ is a member selected from the group consisting of alkyl, aryl, arylalkyl and bicyclic fused aryl-cycloalkyl;

R$^6$ is a member selected from the group consisting of hydrogen, alkyl, aryl and arylalkyl; or is combined with

53

R⁵ and the nitrogen atom to which R⁵ and R⁶ are attached to form a 5-, 6-, 7- or 8-membered aromatic or non-aromatic ring containing one to three heteroatoms selected from the group consisting of N, O or S;

R⁷ and R⁸ are members independently selected from the group consisting of hydrogen, alkyl, aryl and arylalkyl;

R⁹ and R¹⁰ are members independently selected from the group consisting of hydrogen, alkyl, aryl and arylalkyl;

R¹¹ is a member selected from the group consisting of alkyl, aryl and arylalkyl;

m is an integer of from 1 to 2;

n is an integer of from 1 to 3; and wherein R¹ and R³, R⁵ and N¹, or R² and N¹ are joined to form a 5-, 6-, 7-, or 8- membered aromatic or non-aromatic ring containing one to three heteroatoms selected from the group consisting of N, O and S;

said compound having a molecular weight of from about 150 to about 750, with the proviso that when Y is a bond, then R⁵ is other than an imidazole ring.

2. A compound in accordance with claim 1, wherein R¹ is selected from the group consisting of —NO₂, —S(O)ₘNR⁷R⁸, —S(O)ₙR⁹, —CN, fluoroalkyl, —C(O)R⁹, —CO₂R¹⁰ and —C(O)NR⁷R⁸ and R² is selected from the group consisting of hydrogen, alkyl, —O-alkyl, —S-alkyl, aryl, arylalkyl, —O-aryl and —S-aryl.

3. A compound in accordance with claim 2, wherein X is —NR³R⁴, Y is selected from the group consisting of —N(R⁶)—, —O— and —S—, R² is a member selected from the group consisting of hydrogen, alkyl, —O-alkyl and halogen.

4. A compound in accordance with claim 3, wherein R¹ is selected from the group consisting of —CF₃, —S(O)ₘNR⁷R⁸, —CO₂R¹⁰, —CN and —NO₂, and R² is selected from the group consisting of hydrogen, (lower)alkyl, —O—(lower)alkyl and —S—(lower)alkyl.

5. A compound in accordance with claim 4, wherein Y is —N(R⁶)— or —O—, R¹ is —NO₂, and R² is hydrogen or (C₁-C₄)alkyl.

6. A compound in accordance with claim 1, wherein R³ is joined to R⁴ form a 5-membered ring, together with the nitrogen to which both radicals are attached.

7. A pharmaceutical composition comprising a pharmaceutically or diagnostically acceptable compound having the formula:

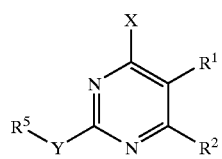

(I)

wherein

X is a member selected from the group consisting of —NR³R⁴, —OR³, —SR³, aryl, alkyl and arylalkyl;

Y is a member selected from the group consisting of a covalent bond, —N(R⁶)—, —O—, —S—, —C(O)— and alkylene;

R¹ and R² are members independently selected from the group consisting of hydrogen, alkyl, —O-alkyl, —S-alkyl, aryl, arylalkyl, —O-aryl, —S-aryl, —NO₂, —NR⁷R⁸, —C(O)R⁹, —CO₂R¹⁰, —C(O)NR⁷R⁸, —N(R⁷)C(O)R⁹, —N(R⁷)CO₂R¹¹, —N(R⁹)C(O)NR⁷R⁸, —S(O)ₘNR⁷R⁸, —S(O)ₙR⁹, —CN, halogen, and —N(R⁷)S(O)ₘR¹¹;

R³ and R⁴ are members independently selected from the group consisting of hydrogen, alkyl, aryl and arylalkyl, or taken together with the nitrogen atom to which each is attached form a 5-, 6- or 7-membered aromatic or non-aromatic ring containing from one to three heteroatoms selected from the group consisting of N, O and S;

R⁵ is a member selected from the group consisting of alkyl, aryl, arylalkyl and bicyclic fused aryl-cycloalkyl;

R⁶ is a member selected from the group consisting of hydrogen, alkyl, aryl and arylalkyl; or is combined with R⁵ and the nitrogen atom to which R⁵ and R⁶ are attached to form a 5-, 6-, 7- or 8-membered aromatic or non-aromatic ring containing one to three heteroatoms selected from the group consisting of N, O or S;

R⁷ and R⁸ are members independently selected from the group consisting of hydrogen, alkyl, aryl and arylalkyl;

R⁹ and R¹⁰ are members independently selected from the group consisting of hydrogen, alkyl, aryl and arylalkyl;

R¹¹ is a member selected from the group consisting of alkyl, aryl and arylalkyl;

m is an integer of from 1 to 2;

n is an integer of from1 to 3; and wherein R¹ and R³, R⁵ and N¹, or R² and N¹ are joined to form a 5-, 6-, 7-, or 8- membered aromatic or non-aromatic ring containing one to three heteroatoms selected from the group consisting of N, O and S;

said compound having a molecular weight of from about 150 to about 750, with the proviso that when Y is a bond, then R⁵ is other than an imidazole ring.

8. A composition in accordance with claim 7, wherein R¹ is selected from the group consisting of —NO₂, —S(O)ₘNR⁷R⁸, —S(O)ₙR⁹, —CN, fluoroalkyl, —C(O)R⁹, —CO₂R¹⁰ and —C(O)NR⁷R⁸ and R² is selected from the group consisting of hydrogen, alkyl, —O-alkyl, —S-alkyl, aryl, arylalkyl, —O-aryl and —S-aryl.

9. A composition in accordance with claim 8, wherein X is —NR³R⁴, Y is selected from the group consisting of —N(R⁶)—, —O— and —S—, R² is a member selected from the group consisting of hydrogen, alkyl, —O-alkyl and halogen.

10. A composition in accordance with claim 9, wherein R¹ is selected from the group consisting of —CF₃, —S(O)ₘNR⁷R⁸, —CO₂R¹⁰, —CN and —NO₂, and R² is selected from the group consisting of hydrogen, (lower)alkyl, —O—(lower)alkyl and —S—(lower)alkyl.

11. A composition in accordance with claim 10, wherein Y is —N(R⁶)— or —O—, R¹ is —NO₂, and R² is hydrogen or (C₁-C₄)alkyl.

12. A compound in accordance with claim 7, wherein R³ is joined to R⁴ to form a 5-membered ring, together with the nitrogen to which both radicals are attached.

* * * * *